(12) United States Patent
Bedingham et al.

(10) Patent No.: US 7,507,575 B2
(45) Date of Patent: Mar. 24, 2009

(54) MULTIPLEX FLUORESCENCE DETECTION DEVICE HAVING REMOVABLE OPTICAL MODULES

(75) Inventors: William Bedingham, Woodbury, MN (US); Peter D. Ludowise, Cottage Grove, MN (US); Barry W. Robole, Woodville, WI (US)

(73) Assignee: 3M Innovative Properties Company, St.Paul, MN (US)

( * ) Notice: Subject to any disclaimer, the term of this patent is extended or adjusted under 35 U.S.C. 154(b) by 249 days.

(21) Appl. No.: 11/174,754

(22) Filed: Jul. 5, 2005

(65) Prior Publication Data

US 2006/0223169 A1 Oct. 5, 2006

Related U.S. Application Data

(60) Provisional application No. 60/667,461, filed on Apr. 1, 2005.

(51) Int. Cl.
*C12M 1/34* (2006.01)
*C12M 1/00* (2006.01)
*C12Q 1/68* (2006.01)

(52) U.S. Cl. .............. 435/287.2; 435/287.1; 435/283.1; 435/6

(58) Field of Classification Search .................. None
See application file for complete search history.

(56) References Cited

U.S. PATENT DOCUMENTS

| | | | |
|---|---|---|---|
| 3,949,231 A | 4/1976 | Blunck et al. ............... 250/493 |
| 4,343,991 A | 8/1982 | Fujiwara et al. ............. 250/227 |
| 4,726,676 A * | 2/1988 | Maslaney et al. .......... 356/73.1 |
| 4,909,990 A | 3/1990 | Block et al. .............. 422/82.11 |
| 4,927,766 A | 5/1990 | Auerbach et al. ............. 436/44 |
| 5,296,958 A * | 3/1994 | Roddy et al. ................ 359/204 |
| 5,414,600 A | 5/1995 | Strobl et al. ................... 362/32 |
| 5,473,437 A | 12/1995 | Blumenfeld et al. ......... 356/417 |
| 5,585,069 A | 12/1996 | Zanzucchi et al. ........... 422/100 |
| 5,639,668 A | 6/1997 | Neel et al. ................... 436/172 |
| 5,751,874 A * | 5/1998 | Chudoba et al. ............... 385/72 |
| 5,766,889 A | 6/1998 | Atwood ..................... 435/91.2 |
| 5,928,907 A | 7/1999 | Woudenberg et al. ...... 435/91.2 |

(Continued)

FOREIGN PATENT DOCUMENTS

DE    2 055 944    5/1972

(Continued)

OTHER PUBLICATIONS

Definition from m-w.com.*

(Continued)

*Primary Examiner*—B J Forman
*Assistant Examiner*—Robert T. Crow

(57) ABSTRACT

Techniques are described for the detection of multiple target species in real-time PCR (polymerase chain reaction). For example, a system comprises a data acquisition device and a detection device coupled to the data acquisition device. The detection device includes a rotating disk having a plurality of process chambers having a plurality of species that emit fluorescent light at different wavelengths. The device further includes a plurality of removable optical modules. Each of the removable optical modules is optically configured to excite the species and capture fluorescent light emitted by the species at different wavelengths. A fiber optic bundle coupled to the plurality of removable optical modules conveys the fluorescent light from the optical modules to a single detector.

36 Claims, 23 Drawing Sheets

U.S. PATENT DOCUMENTS

| | | | |
|---|---|---|---|
| 5,994,150 A | 11/1999 | Challener et al. ............ 436/518 |
| 6,015,674 A | 1/2000 | Woudenberg et al. .......... 435/6 |
| 6,144,448 A | 11/2000 | Mitoma ...................... 356/317 |
| 6,161,946 A | 12/2000 | Bishop et al. |
| 6,232,075 B1* | 5/2001 | Williams ........................ 435/6 |
| 6,339,473 B1 | 1/2002 | Gordon ...................... 356/440 |
| 6,342,349 B1 | 1/2002 | Virtanen ........................ 435/6 |
| 6,442,116 B2* | 8/2002 | Asano .................... 369/47.28 |
| 6,537,211 B1* | 3/2003 | Wang et al. ................. 600/178 |
| 6,563,113 B1* | 5/2003 | Amann et al. ............... 250/309 |
| 6,563,581 B1 | 5/2003 | Oldham et al. .............. 356/317 |
| 6,597,450 B1 | 7/2003 | Andrews et al. ............. 356/317 |
| 6,597,832 B2* | 7/2003 | Cheng .......................... 385/25 |
| 6,616,304 B2 | 9/2003 | Li ................................ 362/302 |
| 6,627,159 B1 | 9/2003 | Bedingham et al. ......... 422/100 |
| 6,734,401 B2 | 5/2004 | Bedingham et al. ......... 219/388 |
| 6,803,999 B1 | 10/2004 | Gordon ......................... 356/73 |
| 6,806,954 B2 | 10/2004 | Sandstrom .................. 356/317 |
| 6,821,771 B2 | 11/2004 | Festoc ........................ 435/287 |
| 6,833,536 B2 | 12/2004 | Shigeura .................... 219/553 |
| 6,992,278 B2 | 1/2006 | Sjoberg et al. .............. 250/231 |
| 6,992,769 B2 | 1/2006 | Gordon ...................... 356/440 |
| 7,088,650 B1* | 8/2006 | Worthington et al. .... 369/47.15 |
| 7,238,269 B2 | 7/2007 | Gason et al. |
| 7,322,254 B2 | 1/2008 | Bedingham et al. |
| 2001/0029036 A1 | 10/2001 | Landers et al. ............. 435/91.1 |
| 2001/0046712 A1* | 11/2001 | Hang et al. .................. 436/172 |
| 2001/0052927 A1* | 12/2001 | Takase et al. ............... 347/257 |
| 2002/0039333 A1* | 4/2002 | Tsukahara et al. ....... 369/44.36 |
| 2002/0043626 A1 | 4/2002 | Booker et al. ............... 250/459 |
| 2002/0047003 A1* | 4/2002 | Bedingham et al. ......... 219/388 |
| 2002/0048533 A1 | 4/2002 | Harms et al. .................. 422/99 |
| 2002/0064885 A1 | 5/2002 | Bedingham et al. ......... 436/174 |
| 2002/0076354 A1 | 6/2002 | Cohen ......................... 422/72 |
| 2002/0104884 A1* | 8/2002 | Meier et al. ............ 235/462.25 |
| 2002/0172980 A1* | 11/2002 | Phan et al. .................... 435/7.1 |
| 2003/0054563 A1 | 3/2003 | Ljungstrom et al. ......... 436/172 |
| 2003/0190184 A1* | 10/2003 | O'Brien et al. ............. 403/122 |
| 2003/0219754 A1 | 11/2003 | Oleksy et al. .................. 435/6 |
| 2004/0067051 A1 | 4/2004 | Kylberg et al. .............. 392/407 |
| 2004/0072335 A1 | 4/2004 | Boege et al. ................ 435/287 |
| 2004/0126279 A1* | 7/2004 | Renzi et al. .................. 422/100 |
| 2004/0224317 A1 | 11/2004 | Kordunsky et al. ............. 435/6 |
| 2005/0012199 A1* | 1/2005 | Rosenau et al. ............. 257/696 |
| 2005/0014249 A1 | 1/2005 | Staimer et al. .............. 435/287 |
| 2005/0023765 A1 | 2/2005 | Coombs ..................... 277/345 |
| 2005/0048595 A1 | 3/2005 | Yamatsu et al. ............... 435/18 |
| 2005/0059062 A1 | 3/2005 | Kaiser ........................... 435/6 |
| 2005/0064582 A1 | 3/2005 | Wittwer et al. .............. 435/287 |
| 2005/0074784 A1 | 4/2005 | Vo-Dinh ........................ 435/6 |
| 2005/0109396 A1 | 5/2005 | Zucchelli et al. .............. 137/67 |
| 2005/0130177 A1 | 6/2005 | Bedingham et al. ............ 435/6 |
| 2005/0151972 A1 | 7/2005 | Boege et al. ................ 356/417 |
| 2006/0223169 A1 | 10/2006 | Bedingham et al. ......... 435/287 |
| 2006/0223172 A1 | 10/2006 | Bedingham et al. ......... 435/288 |
| 2007/0009382 A1 | 1/2007 | Bedingham et al. ........... 422/63 |
| 2007/0009383 A1 | 1/2007 | Bedingham et al. ........... 422/63 |
| 2007/0010007 A1 | 1/2007 | Aysta et al. ................. 435/287 |

FOREIGN PATENT DOCUMENTS

| | | |
|---|---|---|
| JP | 61-20839 | 1/1986 |
| WO | WO 91/03915 | 3/1991 |
| WO | WO 98/38510 | 9/1998 |
| WO | WO 01/01112 | 1/2001 |
| WO | WO 02/073605 | 9/2002 |
| WO | WO 03/058253 | 7/2003 |
| WO | WO 03/098278 | 11/2003 |
| WO | WO 03/098279 | 11/2003 |
| WO | WO 03/102226 | 12/2003 |
| WO | WO 2004/079343 | 9/2004 |
| WO | WO 2004/087950 | 10/2004 |

OTHER PUBLICATIONS

Wenner et al.; "Biosensing on the CD Microfluidic Platform with Genetically Engineered Proteins"; Society of Automotive Engineers, Inc.; Paper 2000-01-2513; pp. 1-6; 2000.

Lee et al.; "A novel real-time PCR machine with a miniature spectrometer for fluorescence sensing in a micro liter volume glass capillary"; Sensors and Actuators B 100 (2004) 401-410.

Lee et al.; "Development of a CCD-based fluorimeter for real-time PCR machine"; Sensors and Actuators B 107 (2005) 872-881.

* cited by examiner

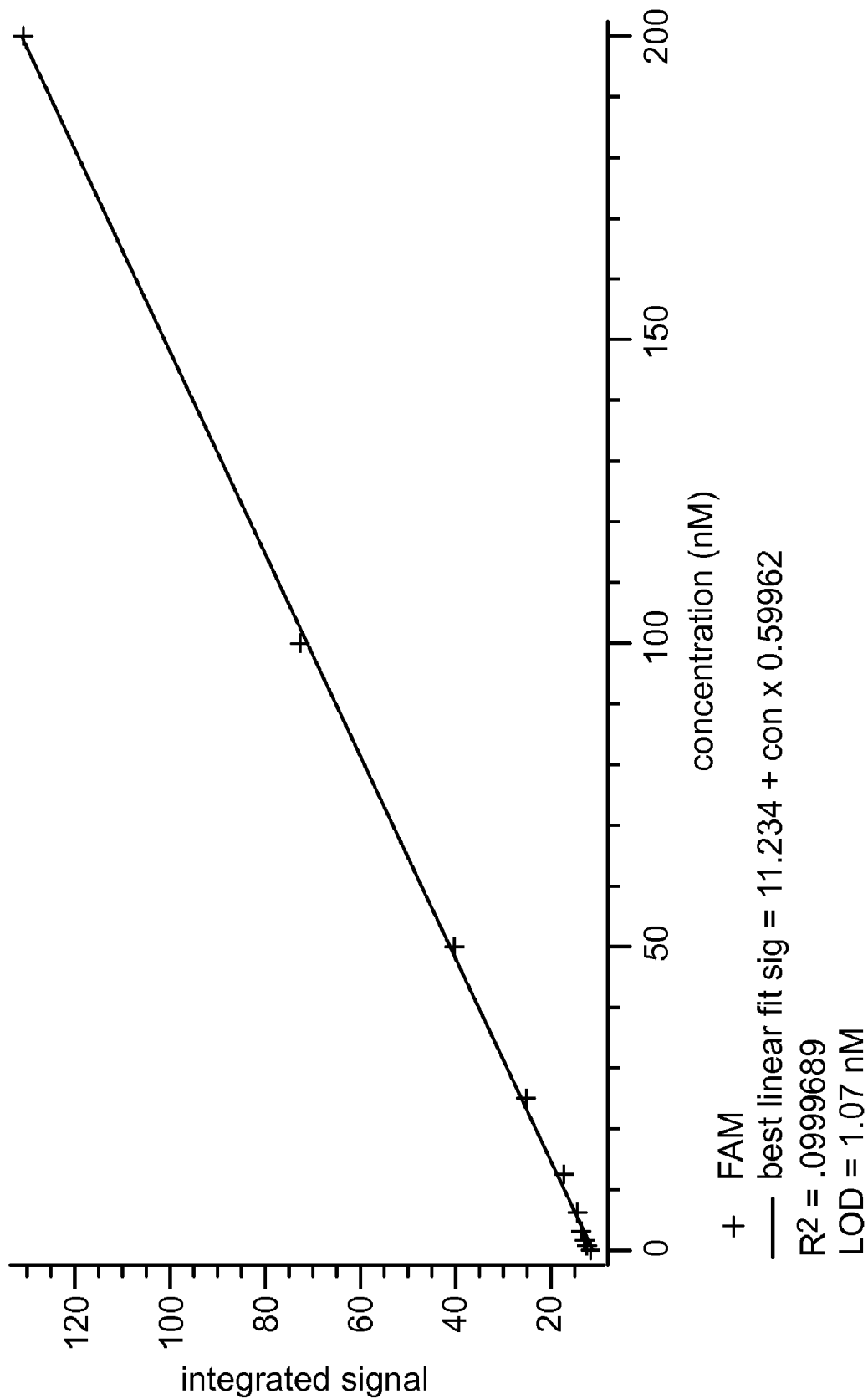

MULTIPLEX FLUORESCENCE DETECTION DEVICE HAVING REMOVABLE OPTICAL MODULES

CROSS REFERENCE TO RELATED APPLICATIONS

This application claims the benefit of U.S. Provisional Application No. 60/667,461, filed Apr. 1, 2005, the entire content of which is incorporated herein by reference.

TECHNICAL FIELD

The invention relates to assaying systems and, more particularly, techniques for the detection of multiple target species using fluorescent dyes.

BACKGROUND

Optical disc systems are often used to perform various biological, chemical or bio-chemical assays. In a typical system, a rotatable disc is used as a medium for storing and processing fluid specimens, such as blood, plasma, serum, urine or other fluid.

One type of analysis is polymerase chain reaction (PCR), which is often used for nucleic acid sequence analysis. In particular, PCR is often used for DNA sequencing, cloning, genetic mapping, and other forms of nucleic acid sequence analysis.

In general, PCR relies on the ability of DNA-copying enzymes to remain stable at high temperatures. There are three major steps in PCR: denaturation, annealing, and extension. During the denaturation, a liquid sample is heated at approximately 94° C. During this process, double DNA strands "melt" open into single stranded DNA and all enzymatic reactions stop. During annealing, the single stranded DNA is cooled to 54° C. At this temperature, primers bind or "anneal" to the ends of the DNA strands. During extension, the sample is heated to 75° C. At this temperature, nucleotides add to the primers and eventually a complementary copy of the DNA template is formed.

There are a number of existing PCR instruments designed to determine levels of specific DNA and RNA sequences in the sample during the PCR in real-time. Many of the instruments are based on the use of fluorescent dyes. In particular, many conventional real-time PCR instruments detect a fluorescent signal produced proportionally during amplification of a PCR product.

Conventional real-time PCR instruments use different methods for detection of different fluorescent dyes. For example, some conventional PCR instruments incorporate white light sources with filter wheels for spectrally resolving each dye. The white light sources are tungsten halogen bulbs, which have a lifetime maxima of a few thousand hours. The filter wheels are typically complicated electromechanical parts that are susceptible to wear.

SUMMARY

In general, the invention relates to techniques for the detection of multiple target species in real-time PCR (polymerase chain reaction), referred to herein as multiplex PCR. In particular, a multiplex fluorescence detection device is described that incorporates a plurality of optical modules. Each of the optical modules may be optimized for detection of a respective fluorescent dye at a discrete wavelength band. In other words, the optical modules may be used to interrogate multiple, parallel reactions at different wavelengths. The reaction may, for example, occur within a single process chamber (e.g., well) of a rotating disk. Additionally, each optical module may be removable to quickly change the detection capabilities of the device.

The plurality of optical modules may be optically coupled to a single detector by a multi-legged optical fiber bundle. In this manner, multiplexing can be achieved by using a plurality of optical modules and a single detector, e.g., a photomultiplier tube. The optical components in each optical module may be selected to maximize sensitivity and minimize the amount of spectral crosstalk, i.e., signals from one dye on another optical module.

In one embodiment, a device comprises a motor to rotate a disk having a plurality of process chambers each holding a respective sample and a plurality of fluorescent dyes, a plurality of optical modules, and a housing having a plurality of locations adapted to receive the optical modules wherein each of the optical modules includes an optical channel having a light source selected for a different one of the dyes and a lens to capture fluorescent light emitted from the disk.

In another embodiment, a system comprises a data acquisition device. The system further comprises a detection device coupled to the data acquisition device, wherein the detection device comprises a motor to rotate a disk having a plurality of process chambers each holding a respective sample and a plurality of fluorescent dyes, a plurality of optical modules, and a housing having a plurality of locations adapted to receive the optical modules wherein each of the optical modules includes an optical channel having a light source selected for a different one of the dyes and a lens to capture fluorescent light emitted from the disk.

In an additional embodiment, a method comprises rotating a disk having a plurality of process chambers each having a plurality of species that emit fluorescent light at different wavelengths, exciting the disk with a plurality of light beams to produce a plurality of emitted fluorescent light beams, capturing the fluorescent light beams with a plurality of different optical modules, wherein the modules are optically configured for the different wavelengths, containing the plurality of different modules within a housing.

The invention may provide one or more advantages. For example, the modular design may allow a technician to quickly and efficiently interchange detection modules depending on the particular reactions being performed. Moreover, the technician may select detection modules that are optically optimized for different reactions. Further, different combinations of detection modules may be installed and utilized within the real-time, multiplex PCR device.

While the device may be capable of conducting real-time PCR, the device may be capable of analyzing any type of biological reaction while it occurs. The device may be able to modulate the temperature of each reaction independently or as a selected group, and the device may be able to support multiple stages of reactions by including a valve between two chambers. This valve may be opened during reactions through the use of a laser which delivers a burst of energy to the valve.

In some embodiments, the device may be portable and robust to allow operation in remote areas or temporary laboratories. The device may include a data acquisition computer for analyzing the reactions in real-time, or the device may communicate the data to another device through wired or wireless communication interfaces.

The details of one or more embodiments of the invention are set forth in the accompanying drawings and the descrip-

BRIEF DESCRIPTION OF DRAWINGS

FIGS. 16A and 16B show a limit of detection (LOD) for the data received from two exemplary detection modules.

DETAILED DESCRIPTION

Figure 1:
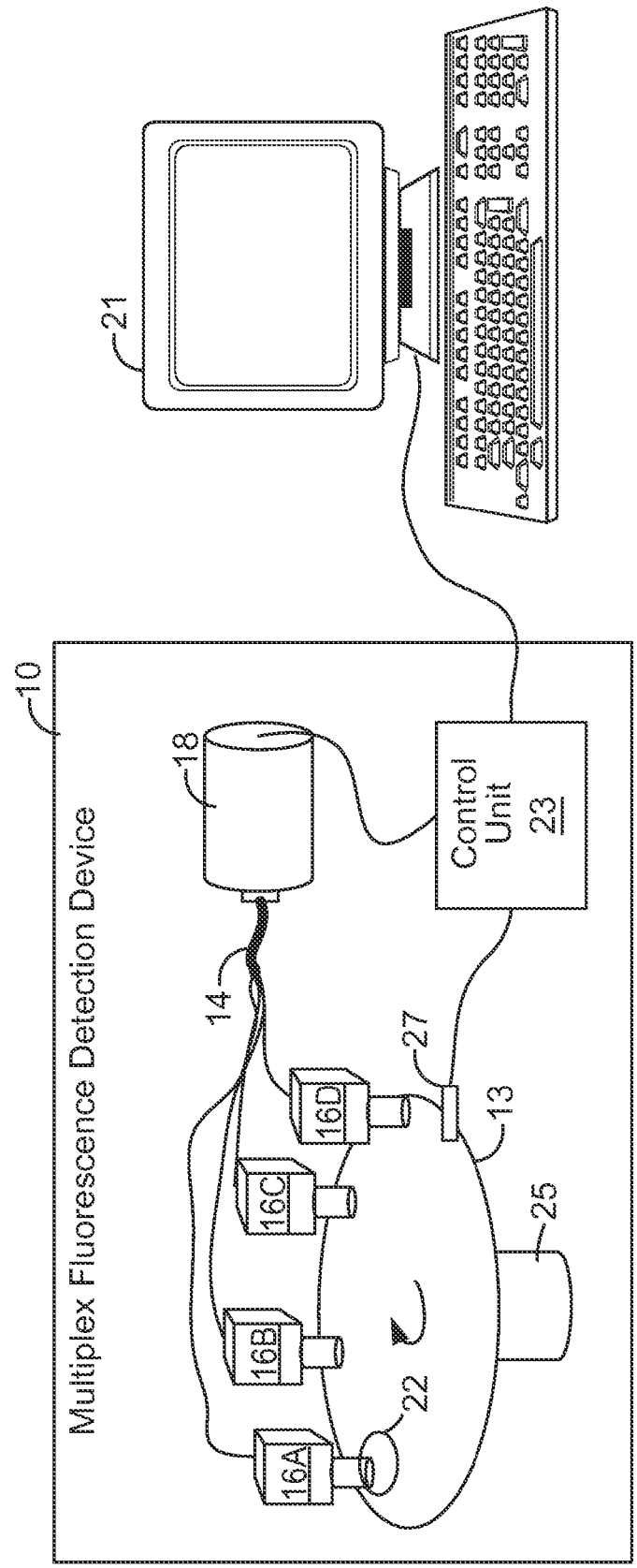
FIG. 1 is a block diagram illustrating an exemplary embodiment of a multiplex fluorescence detection device.

FIG. 1 is a block diagram illustrating an exemplary embodiment of a multiplex fluorescence detection device 10. In the illustrated example, device 10 has four optical modules 16 that provide four "channels" for optical detection of four different dyes. In particular, device 10 has four optical modules 16 that excite different regions of rotating disk 13 at any given time, and collect emitted fluorescent light energy at different wavelengths from the dyes. As a result, modules 16 may be used to interrogate multiple, parallel reactions occurring within sample 22.

The multiple reactions may, for example, occur simultaneously within a single chamber of a rotating disk 13. Each of optical modules 16 interrogates sample 22 and collects fluorescent light energy at different wavelengths as the disk 13 rotates. For example, excitation sources within modules 16 may be sequentially activated for periods sufficient to collect data at the corresponding wavelengths. That is, an optical module 16A may be activated for a period of time to collect data at a first range of wavelengths selected for a first dye corresponding to a first reaction. The excitation source may then be deactivated, and an excitation source within module 16B may be activated to interrogate sample 22 at a second range of wavelengths selected for a second dye corresponding to a second reaction. This process continues until data has been captured from all optical modules 16. In one embodiment, each of the excitation sources within optical modules 16 is activated for an initial period of approximately two seconds to reach steady state followed by an interrogation period which lasts for 10-50 rotations of disk 13. In other embodiments, the excitation sources may be sequenced for shorter (e.g., 1 or 2 milliseconds) or longer periods. In some embodiments, more than one optical module may be activated simultaneously for concurrent interrogation of sample 22 without stopping the rotation of disk 13.

Although a single sample 22 is illustrated, disk 13 may contain a plurality of chambers holding samples. Optical modules 16 may interrogate some or all of the different chambers at different wavelengths. In one embodiment, disk 13 includes 96 chambers space around a circumference of disk 13. With a 96 chamber disk and four optical modules 16, device 10 may be capable of acquiring data from 384 different species.

In one embodiment, optical modules 16 include excitation sources that are inexpensive high power light emitting diodes (LEDs), which are commercially available in a variety of wavelengths and have long lifetimes (e.g., 100,000 hours or more). In another embodiment, conventional halogen bulbs or mercury lamps may be used as excitation sources.

As illustrated in FIG. 1, each of optical modules 16 may be coupled to one leg of a fiber optic bundle 14. Fiber optic bundle 14 provides a flexible mechanism for collection of fluorescent signals from optical modules 16 without loss of sensitivity. In general, a fiber optic bundle comprises multiple optical fibers laid side by side and bonded together at the ends and encased in a flexible protective jacket. Alternatively, fiber optic bundle 14 may comprise a smaller number of discrete, large diameter multimode fibers, either glass or plastic, having a common end. For example, for a four-optical module device, fiber optic bundle 16 may comprise four discrete multimode fibers, each having a 1 mm core diameter. The common end of the bundle contains the four fibers bound together. In this example, the aperture of detector 18 may be 8 mm, which is more than sufficient for coupling to the four fibers.

In this example, fiber optic bundle 14 couples optical modules 16 to a single detector 18. The optical fibers carry the fluorescent light collected by optical modules 16 and effectively deliver the captured light to detector 18. In one embodiment, detector 18 is a photomultiplier tube. In another embodiment, the detector may include multiple photomultiplier elements, one for each optical fiber, within the single detector. In other embodiments, one or more solid-state detectors may be used.

The use of a single detector 18 may be advantageous in that it allows use of a highly sensitive and possibly expensive detector (e.g., a photomultiplier), while maintaining a minimal cost in that only a single detector need be used. A single detector is discussed herein; however, one or more detectors may be included for detecting a greater number of dyes. For example, four additional optical modules 16 and a second detector may be added to the system to allow for the detection of eight different wavelengths emitted from one disk. An exemplary fiber optic bundle coupled to a single detector for use with rotating disk 13 is described in U.S. patent application Ser. No. 11/174,755, entitled "MULTIPLEX FLUORESCENCE DETECTION DEVICE HAVING FIBER BUNDLE COUPLING MULTIPLE OPTICAL MODULES TO A COMMON DETECTOR," filed on Jul. 5, 2005, the entire content of which is hereby incorporated by reference.

Optical modules 16 are removable from the device and easily interchangeable with other optical modules that are optimized for interrogation at different wavelengths. For example, optical modules 16 may be physically mounted within locations of a module housing. Each of optical modules 16 may be easily inserted within a respective location of the housing along guides (e.g., recessed grooves) that mate with one or more marking (e.g., guide pins) of the optical module. Each optical module includes an optical output port (shown in FIGS. 6A and 7A) for coupling to one leg of fiber optic bundle 14. The optical output port may have a threaded end coupled to a threaded connector of the leg. Alternatively, a form of "quick-connect" may be used (e.g., a slidable connection having an o-ring and a catch pin) that allows fiber optic bundle 14 to be slidably engaged and disengaged from the optical output port. Moreover, each of optical modules 16 may have one or more electrical contacts for electronically coupling to control unit 23 when fully inserted.

The modular architecture of device 10 allows the device to be easily adapted for all of the fluorescent dyes used in a given analysis environment, such as multiplex PCR. Other chemistries that may be used in device 10 include Invader (Third Wave, Madison, Wis.), Transcripted-mediated Amplification (GenProbe, San Diego, Calif.), fluorescence labeled enzyme linked immunosorbent assay (ELISA) or fluorescence in situ hybridization (FISH). The modular architecture of device 10 may provide another advantage in that the sensitivity of each optical module 16 can be optimized by choice of the corresponding excitation source (not shown) and excitation and detection filters for a small specific target range of wavelengths in order to selectively excite and detect a corresponding dye in the multiplex reaction.

For purpose of example, device 10 is illustrated in a 4-color multiplex arrangement, but more or less channels can be used with the appropriate fiber optic bundle 14. This modular design allows a user to easily upgrade device 10 in the field by simply adding another optical module 16 to base 20 and inserting one leg of fiber optic bundle 14 into the new optical module. Optical modules 16 may have integrated electronics that identify the optical modules and download calibration data into an internal control module or other internal electronics (e.g., control unit 23) of device 10.

In the example of FIG. 1, samples 22 are contained in chambers of disk 13, which is mounted on a rotating platform under the control of control unit 23. A slot sensor trigger 27 provides an output signal utilized by control unit 23 and data acquisition device 21 for synchronizing data acquisition with chamber position during disk rotation. Slot sensor trigger 27 may be a mechanical or optical sensor. For example, the sensor may be a laser which sends a beam of light to disk 13 and control unit 23 uses a sensor detecting light passing through a slot in disk 13 to locate the chambers on the disk. In other embodiments, disk 13 may include a tab, protrusion or reflective surface in addition to or in place of the slot. Slot sensor trigger 27 may use any physical structure or mechanism to locate the radial position of disk 13 as it rotates. Optical modules 16 may be physically mounted above rotating platform 25. As a result, optical modules 16 are overlapped with different chambers at any one time.

Detection device 10 also includes a heating element (not shown) for modulating the temperature of the sample 22 on disk 13. The heating element may comprise a cylindrical halogen bulb contained within a reflective enclosure. The reflective chamber is shaped to focus radiation from the bulb onto a radial section of disk 13. Generally, the heated area of disk 13 would resemble a ring as disk 13 spins. In this embodiment, the shape of the reflective enclosure may be a combination of elliptical and spherical geometries that allow precise focusing. In other embodiments, the reflective enclosure may be of a different shape or the bulb may broadly irradiate a larger area. In other embodiments, the reflective enclosure may be shaped to focus the radiation from the bulb onto a single area of the disk 13, such as a single process chamber containing a sample 22.

In some embodiments, the heating element may heat air and force the hot air over one or more samples to modulate the temperature. Additionally, the samples may be heated directly by the disk. In this case, the heating element may be located in platform 25 and thermally couple to disk 13. Electrical resistance within the heating element may heat a selected region of the disk as controlled by control unit 23. For example, a region may contain one or more chambers, possibly the entire disk. An exemplary heating element for use with rotating disk 13 is described in U.S. patent application Ser. No. 11/174,691, entitled "HEATING ELEMENT FOR A ROTATING MULTIPLEX FLUORESCENCE DETECTION DEVICE," filed on Jul. 5, 2005, the entire content of which is hereby incorporated by reference.

Alternatively, or in addition, device 10 may also includes a cooling component (not shown). A fan is included in device 10 to supply cold air, i.e., room temperature air, to disk 13. Cooling may be needed to modulate the temperature of the sample appropriately and store samples after an experiment has completed. In other embodiments, the cooling component may include thermal coupling between platform 25 and disk 13, as platform 25 may reduce its temperature when needed. For example, some biological samples may be stored at 4 degrees Celsius to reduce enzyme activity or protein denaturing.

Detection device 10 may also be capable of controlling reaction species contained within a process chamber. For example, it may be beneficial to load some species in a process chamber to generate one reaction and later adding another species to the sample once the first reaction has terminated. A laser homing valve may be added to control a valve position separating an inner holding chamber from the process chamber, thereby controlling the addition of species to the chamber during rotation of disk 13. This laser device may be located within one of optical modules 16 or separate from the optical modules. Directly below the laser, under disk 13, may be a laser sensor for positioning the laser relative to disk 13.

In one embodiment, the laser is a near infrared (NIR) laser with at least two power settings. Under a low power setting, the laser positioning sensor may indicate that the laser is in position over the chamber valve by recognizing the NIR light though a slot in disk 13. Once the laser is in position, control unit 23 directs the laser to output a short burst of high power energy to heat the valve and open it. The open valve may then allow the inner fluid specimen to flow toward from the inside chamber to the outside process chamber and conduct a second reaction. In some embodiments, disk 13 may contain a plurality of valves to generate a plurality of reactions in sequence. More than one set of laser and laser sensor may also be used when utilizing multiple chamber valves. An exemplary laser homing valve control system for use with rotating disk 13 is described in U.S. patent application Ser. No. 11/174,957, entitled "VALVE CONTROL SYSTEM FOR A ROTATING MULTIPLEX FLUORESCENCE DETECTION DEVICE," filed on Jul. 5, 2005, the entire content of which is hereby incorporated by reference.

Data acquisition device 21 may collect data from device 10 for each dye either sequentially or in parallel. In one embodiment, data acquisition system 21 collects the data from optical modules 16 in sequence, and corrects the spatial overlap by a trigger delay for each one of the optical modules measured from slot sensor trigger 27.

One application for device 10 is real-time PCR, but the techniques described herein may be extended to other platforms that utilize fluorescence detection at multiple wavelengths. Device 10 may combine rapid thermal cycling, utilizing the heating element, and centrifugally driven microfluidics for isolation, amplification, and detection of nucleic acids. By making use of multiplex fluorescence detection, multiple target species may be detected and analyzed in parallel.

For real-time PCR, fluorescence is used to measure the amount of amplification in one of three general techniques. The first technique is the use of a dye, such as Sybr Green (Molecular Probes, Eugene, Oreg.), whose fluorescence increases upon binding to double-stranded DNA. The second technique uses fluorescently labeled probes whose fluorescence changes when bound to the amplified target sequence (hybridization probes, hairpin probes, etc.). This technique is similar to using a double-stranded DNA binding dye, but is more specific because the probe will bind only to a certain section of the target sequence. The third technique is the use of hydrolysis probes (Taqman™, Applied BioSystems, Foster City Calif.), in which the exonuclease activity of the polymerase enzyme cleaves a quencher molecule from the probe during the extension phase of PCR, making it fluorescently active.

In each of the approaches, fluorescence is linearly proportional to the amplified target concentration. Data acquisition system 21 measures an output signal from detector 18 (or alternatively optionally sampled and communicated by control unit 23) during the PCR reaction to observe the amplification in near real-time. In multiplex PCR, the multiple targets are labeled with different dyes that are measured independently. Generally speaking, each dye will have different absorbance and emission spectra. For this reason, optical modules 16 may have excitation sources, lenses and related filters that are optically selected for interrogation of sample 22 at different wavelengths.

Some examples of suitable construction techniques or materials that may be adapted for use in connection with the present invention may be described in, e.g., commonly-assigned U.S. Pat. No. 6,734,401 titled "ENHANCED SAMPLE PROCESSING DEVICES SYSTEMS AND METHODS" (Bedingham et al.) and U.S. Patent Application Publication No. US 2002/0064885 titled "SAMPLE PROCESSING DEVICES." Other useable device constructions may be found in, e.g., U.S. Provisional Patent Application Ser. No. 60/214,508 filed on Jun. 28, 2000 and entitled "THERMAL PROCESSING DEVICES AND METHODS"; U.S. Provisional Patent Application Ser. No. 60/214,642 filed on Jun. 28, 2000 and entitled "SAMPLE PROCESSING DEVICES, SYSTEMS AND METHODS"; U.S. Provisional Patent Application Ser. No. 60/237,072 filed on Oct. 2, 2000 and entitled "SAMPLE PROCESSING DEVICES, SYSTEMS AND METHODS"; U.S. Provisional Patent Application Ser. No. 60/260,063 filed on Jan. 6, 2001 and titled "SAMPLE PROCESSING DEVICES, SYSTEMS AND METHODS"; U.S. Provisional Patent Application Ser. No. 60/284,637 filed on Apr. 18, 2001 and titled "ENHANCED SAMPLE PROCESSING DEVICES, SYSTEMS AND METHODS"; and U.S. Patent Application Publication No. US 2002/0048533 titled "SAMPLE PROCESSING DEVICES AND CARRIERS." Other potential device constructions may be found in, e.g., U.S. Pat. No. 6,627,159 titled "CENTRIFUGAL FILLING OF SAMPLE PROCESSING DEVICES" (Bedingham et al.). The entire content of these disclosures are incorporated herein by reference.

Figure 2:
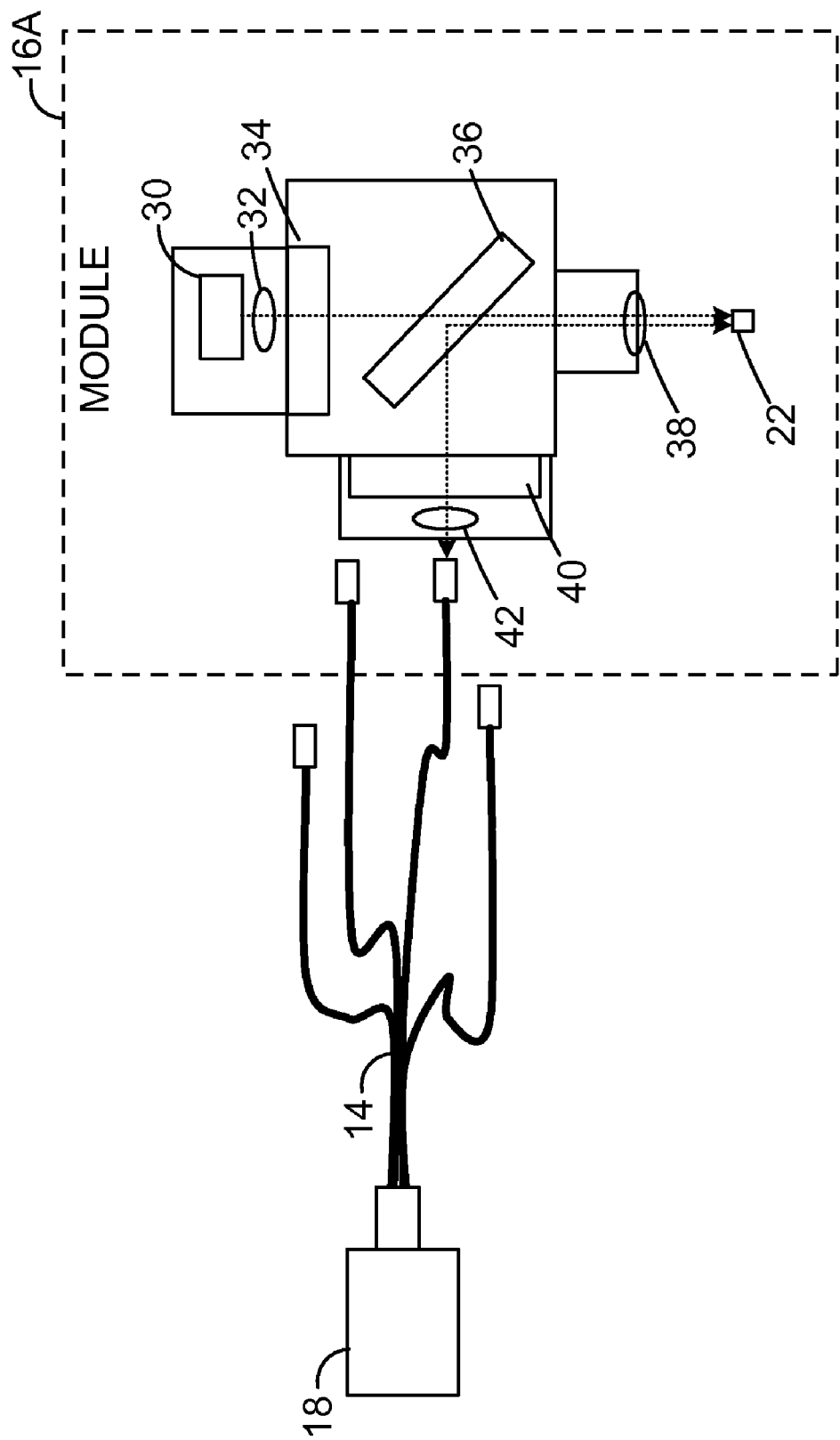
FIG. 2 is a schematic diagram illustrating an exemplary detection module, which may correspond to any of a plurality of detection modules of the fluorescence detection device of FIG. 1.

FIG. 2 is a schematic diagram illustrating an exemplary optical module 16A, which may correspond to any of optical modules 16 of FIG. 1. In this example, optical module 16A contains a high-power excitation source, LED 30, a collimating lens 32, an excitation filter 34, a dichrotic filter 36, a focusing lens 38, a detection filter 40, and a lens 42 to focus the fluorescence into one leg of fiber optic bundle 14.

Consequently, the excitation light from LED 30 is collimated by collimating lens 32, filtered by excitation filter 34, transmitted through dichrotic filter 36, and focused into the sample 22 by focusing lens 38. The resulting fluorescence emitted by the sample is collected by the same focusing lens 38, reflected off of dichrotic filter 36, and filtered by detection filter 40 before focused into one leg of fiber optic bundle 14. The optic bundle 14 then transfers the light to detector 18.

LED 30, collimating lens 32, excitation filter 34, dichrotic filter 36, focusing lens 38, detection filter 40, and lens 42 are selected based on the specific absorption and emission bands of the multiplex dye with which optical module 16A is to be used. In this manner, multiple optical modules 16 may be configured and loaded within device 10 to target different dyes.

Table 1 lists exemplary components that may be used in a 4-channel multiplex fluorescence detection device 10 for a variety of fluorescent dyes. FAM, HEX, JOE, VIC, TET, ROX are trademarks of Applera, Norwalk, Calif. Tamra is a trademark of AnaSpec, San Jose, Calif. Texas Red is a trademark of Molecular Probes. Cy 5 is a trademark of Amersham, Buckinghamshire, United Kingdom.

TABLE 1

| Optical Module | LED | Excitation Filter | Detection Filter | Dye |
| --- | --- | --- | --- | --- |
| 1 | blue | 475 nm | 520 nm | FAM, Sybr Green |
| 2 | green | 530 nm | 555 nm | HEX, JOE, VIC, TET |
| 3 | orange | 580 nm | 610 nm | TAMRA, ROX, Texas Red |
| 4 | red | 630 nm | 670 nm | Cy 5 |

One advantage of the described modular, multiplex detection architecture is the flexibility in optimizing detection for a wide variety of dyes. Conceivably a user may have a bank of several different optical modules that can be plugged into device 10 as needed, of which N can used at any one time, where N is the maximum number of channels supported by the device. Therefore, device 10 and optical modules 16 may be used with any fluorescent dye and PCR detection method. A larger fiber optic bundle may be used to support a larger number of detection channels. Moreover, multiple fiber optic bundles may be used with multiple detectors. For example, two 4-legged fiber optic bundles may be used with eight optical modules 16 and two detectors 18.

Figure 3:
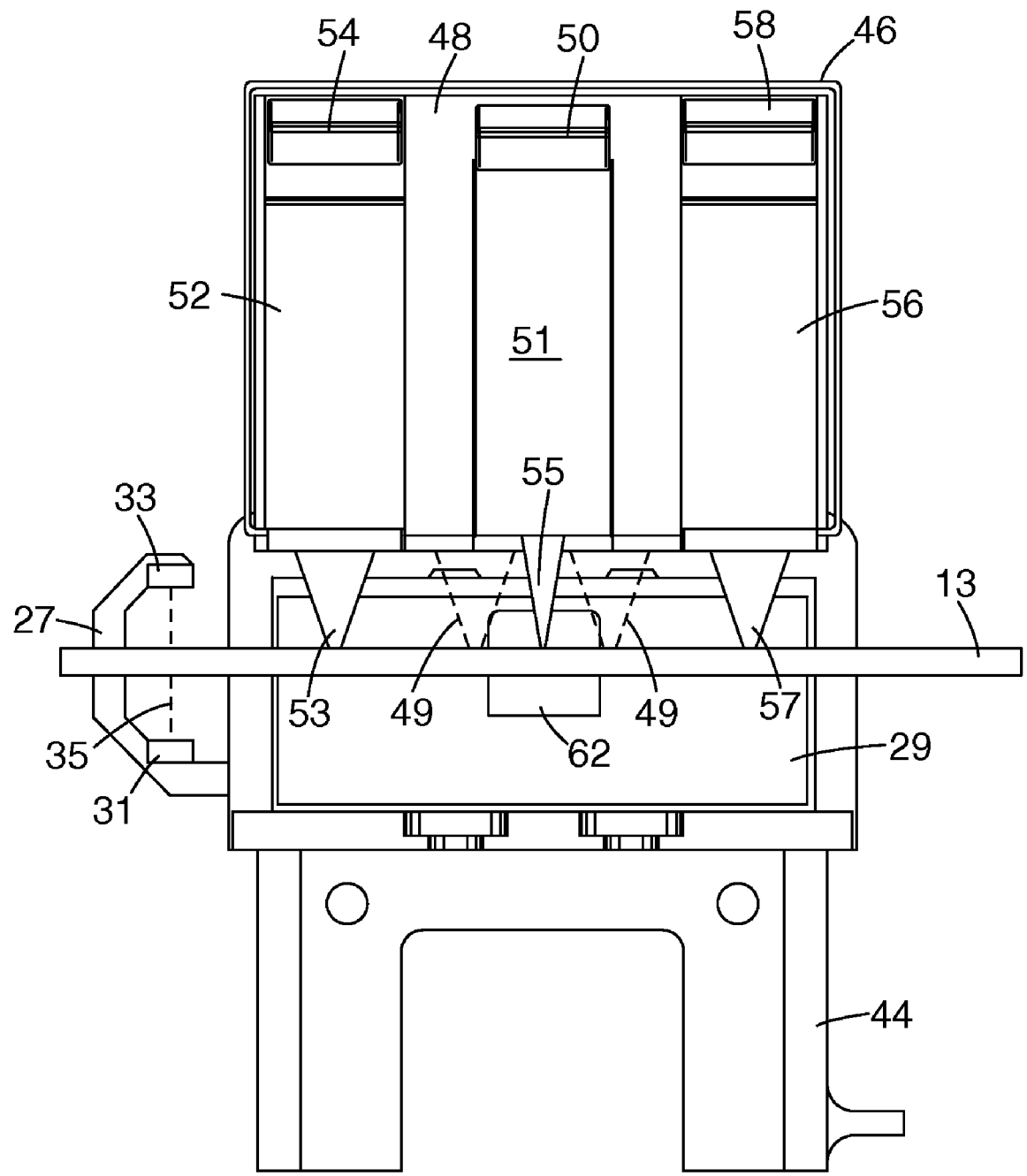
FIG. 3 is a perspective diagram illustrating a front view of an exemplary set of removable optical modules within the device housing.

FIG. 3 is a perspective diagram illustrating a front view of an exemplary set of removable optical modules within the device housing. In the example of FIG. 3, device 10 includes base arm 44 and module housing 46. Main optical module 48, supplemental optical module 52 and supplemental optical module 56 are contained within module housing 46. Optical modules 48, 52 and 56 produce optical output beams 49, 53 and 57, respectively, that sequentially excite different process chambers of disk 13. In other words, output beams 49, 53 and 57 follow the curvature of disk 13 to each excite the same radial position of the disk which contains the process chambers. Slot sensor trigger 27 includes infrared light source 31 which produces light 35 that is detected by detector 33.

Each of optical modules 48, 52 and 56 includes a respective release lever 50, 54 or 58, respectively, for engaging module housing 46. Each release lever may provide an upward bias to engage a respective latch formed within module housing 46. A technician or other user depresses release levers 50, 54 or 58, respectively, in order to unlatch and remove optical module 48, 52 or 56 from module housing 46. Barcode reader 29 includes laser 62 for identifying disk 13.

Base arm 44 extends from detection device 10 and provides support for module housing 46 and optical modules 48, 52 and 56. Module housing 46 may be securely mounted atop base arm 44. Module housing 46 may contain a location adapted to receive a respective one of optical modules 48, 52 and 56. Although described for exemplary purposes with respect to module housing 46, module housing 46 of detection device 10 may have a plurality of locations for receiving optical modules 48, 52 and 56. In other words, a separate housing need not be used for optical modules 48, 52 and 56.

Each location of module housing 46 may contain one or more tracks or guides which help to correctly position the associated optical module within the location when a technician or other user inserts the optical module. These guides may be located along the top, bottom, or sides of each locations. Each of optical modules 48, 52 and 56 may include guides or tracks that mate with the guides or tracks of the locations of module housing 46. For example, module housing 46 may have protruding guides which mate with recessed guides in optical modules 48, 52 and 56.

In some embodiments, module housing 46 may not completely enclose each of optical modules 48, 52 and 56. For example, module housing 46 may provide mounting points to secure each of optical modules 48, 52 and 56 to base arm 44, but portions or all of each optical module may be exposed. In other embodiments, module housing 46 may completely enclose each of optical modules 48, 52 and 56. For example, module housing 46 may include a single door that closes over optical modules 48, 52 and 56, or a respective door for each of the modules. This embodiment may be appropriate for applications where the modules are seldom removed or detection device 10 is subjected to extreme environmental conditions.

A technician may easily remove any of optical modules 48, 52 or 56, and may be completed by using only one hand. For example, the technician may rest his or her forefinger under a molded lip located beneath release lever 54 of optical module 52. The technician's thumb may then press down release lever 54 to release optical module 52 from module housing 46. While grasping optical module 52 between the thumb and forefinger, the technician may pull back on the optical module to remove the optical module from detection device 10. Other methods may be used to remove any of optical module 48, 52 or 56, including methods utilizing two-handed removal. Inserting any of optical module 48, 52 or 56 may be accomplished in a reversed manner with one or two hands.

In the example of FIG. 3, the components of two optical modules are combined to form main optical module 48. Main optical module 48 may contain light sources that produce two different wavelengths of light and detectors for detecting each different wavelength of fluorescence from the samples in disk 13. Therefore, main optical module 48 may connect to two legs of fiber optic bundle 14. In this manner, main optical module 48 may be viewed as a dual-channeled optical module having two independent optical excitation and collection channels. In some embodiments, main optical module 48 may contain optical components for more than two optical modules. In other cases, module housing 46 contains a plurality (e.g., two or more) of single-channeled optical modules, such as supplemental optical modules 52 and 56.

As illustrated in FIG. 3, main optical module 48 may also contain components for a laser valve control system 51 (located within optical module 48). Laser valve control system 51 detects disk 13 location by a small slot located near the outer edge of disk 13. A detector (not shown) detects low power laser light 55 to map the location of disk 13 with respect to the motor which spins the disk. The control unit 23 uses the map to locate valves (not shown) on disk 13.

Laser valve control system 51 focuses laser light 55 on the valves that separate holding chambers towards the center of disk 13 from process chambers near the outer edge of disk 13. When the contents of the holding chambers are to be moved to the associated process chambers, laser valve control system 51 applies laser light 55 to heat a valve separating the chambers, causing the value open and providing fluid communication between the two chambers. In particular, once the valve is open, the contents from the inner holding chamber may then flow towards the outer process chamber as disk 13 is spinning. Detection device 10 may then monitor the subsequent reaction in the process chamber. Contents within a chamber may include substances in a fluid or solid state.

In some embodiments, laser valve control system 51 may be contained within a single-channeled optical module, e.g., supplemental optical module 54 or supplemental optical module 56. In other embodiments, laser valve control system 51 may be mounted to detection device 10 separately from any of optical modules 48, 52 or 56. In this case, laser valve control system 51 may be removable and adapted to engage a location within module housing 46 or a different housing of detection device 10.

In the example of FIG. 3, slot sensor trigger 27 is located near the removable modules, on either side of disk 13. In one embodiment, slot sensor trigger 27 contains a light source 31 to emit infrared (IR) light 35. Detector 33 detects IR light 35 when the slot in disk 13 allows the light to pass through the disk to detector 33. Control unit 23 may use this information to synchronize disk 13 location as it is spinning with data from optical modules 48, 54 and 56. In some embodiments, slot sensor trigger 27 may extend from base arm 44 to reach the outer edge of disk 13 during device 10 operation. In other embodiments, a mechanical detector may be used to detect the position of disk 13.

Barcode reader 29 uses laser 62 to read a barcode located on the side edge of disk 13. The barcode identifies the type of disk 13 to allow proper operation of device 10. In some embodiments, the barcode may identify the actual disk to assist a technician in tracking data to specific samples from multiple disks 13.

All surface components of optical modules 48, 52 and 56 may be constructed of a polymer, composite, or metal alloy. For example, high molecular weight polyurethane may be used in forming the surface components. In other cases, an aluminum alloy or carbon fiber structure may be created. In any case, the material may be resistant to heat, fatigue, stress, and corrosion. As detection device 10 may come into contract with biological materials, the structures may be sterilizable in the event chamber contents leak out of disk 13.

Figure 4:
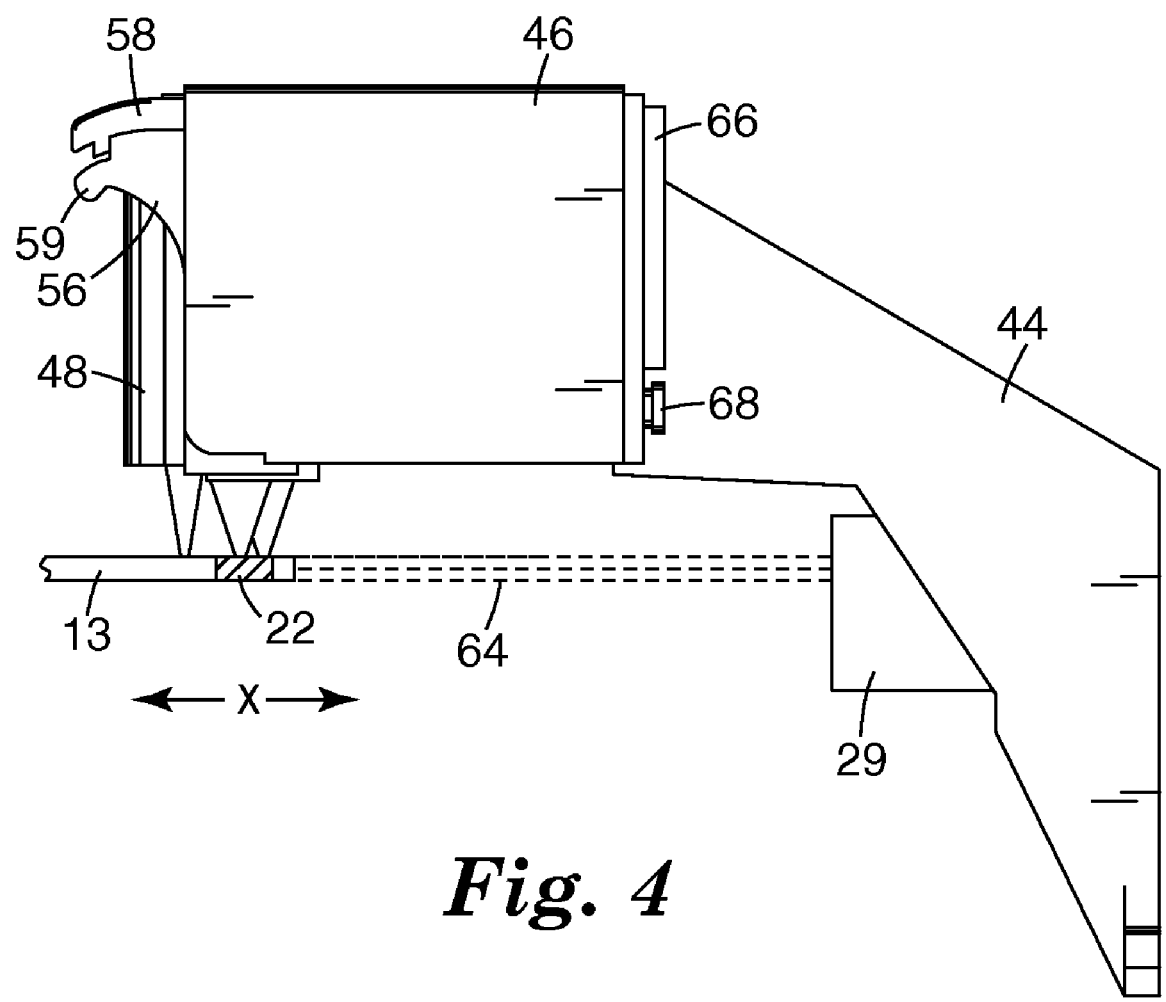
FIG. 4 is a perspective diagram illustrating the exemplary set of removable optical modules within the device housing.

FIG. 4 is an perspective diagram illustrating the exemplary set of removable optical modules 48, 52 and 56 within module housing 46 of detection device 10. In the example of FIG. 4, base arm 44 supports barcode reader 29 as well as the removable optical modules 48, 52 and 56 attached within module housing 46. Disk 13 is located beneath optical modules 48, 52 and 56 with the process chambers located under a respective optical path of each of the modules at different moments in time.

Within module housing 46, the fronts of supplementary module 56 and main optical module 48 can be seen. Supplementary module 56 contains molded lip 59 and release lever 58. As previously described, molded lip 59 may be used to grasp module 56 when removing or inserting the module into module housing 46. All of optical modules 48, 52 and 56 may have a respective molded lip and release lever, or a single release lever may be used to remove all of the optical modules. In some embodiments, optical modules 48, 52 and 56 may contain a different component for grasping the module. For example, each of optical modules 48, 52 and 56 may contain a handle for removing the respective module in a vertical or horizontal direction from module housing 46.

The location of optical modules 48, 52 and 56 within module housing 46 may be fixed in order to separately excite different samples within disk 13 at any particular moment in time. For example, main optical module 48 may be located slightly further toward base arm 44 than supplemental optical modules 52 and 56, which are offset to a location at either side of the main module. Moreover, optical modules 48, 52 and 56 may be offset in a horizontal direction (indicated by the arrow in FIG. 4, where X is the distance the outside light beams are offset from the inside light beams) so that the excitation light beams produced by the modules follows the curvature of disk 13. In this arrangement, the light beams produced by optical modules 48, 52 and 56 traverse the same path as disk 13 rotates, thereby exciting and collecting light from process chambers located along the path. In other embodiments, optical modules 48, 52 and 56 are aligned such that the excitation light beams traverse different paths around rotating disk 13.

In this example, base arm 44 contains electrical contact board 66 which extends into module housing 46. Inside module housing 46, electrical contact board 66 may contain electrical contacts for each of optical modules 48, 52 and 56. Electrical contact board 66 may be electrically coupled to control unit 23. In some embodiments, each of optical modules 48, 52 and 56 may have a separate associated electrical contact board which is connected to control unit 23.

Fiber optic coupler 68 couples one leg of the fiber optic bundle 14 to an optical output port of optical module 56. Although not shown, each of optical modules 48, 52 and 56 include an optical output port adapted to engage a respective fiber optic coupler mounted to module housing 46. The connection between fiber optic coupler 68 and the leg of fiber optic bundle 14 may be a threaded screw lock, snap closure or friction fit.

Barcode reader 29 produces laser light 64 for reading the barcode of disk 13. The laser light 64 follows a direct path where it interacts with the outer edge of disk 13. The light 64 may spread out to cover a large area of disk 13 at one time. Barcode reader 29 reads the barcode on disk 13 when the disk is rotating at slow speeds. In other embodiments, barcode reader 29 may read the barcode periodically during operation to make sure a new disk has not been loaded in device 10. The barcode reader 29 may detect more than one barcode on disk 13 in other embodiments.

In some embodiments, base arm 44 may be movable with respect to disk 13. In this case, base arm 44 could be configurable to detect samples on different sized disks or samples located within an interior of disk 13. For example, a larger disk containing more process chambers or larger process chambers may be used by moving the base arm 44 further away from the center of disk 13. Module housing 46 may also have a configurable position for each of optical module 48, 52 or 56 so that each module may be movable to one or more circular paths of process chambers around disk 13.

Figure 5:
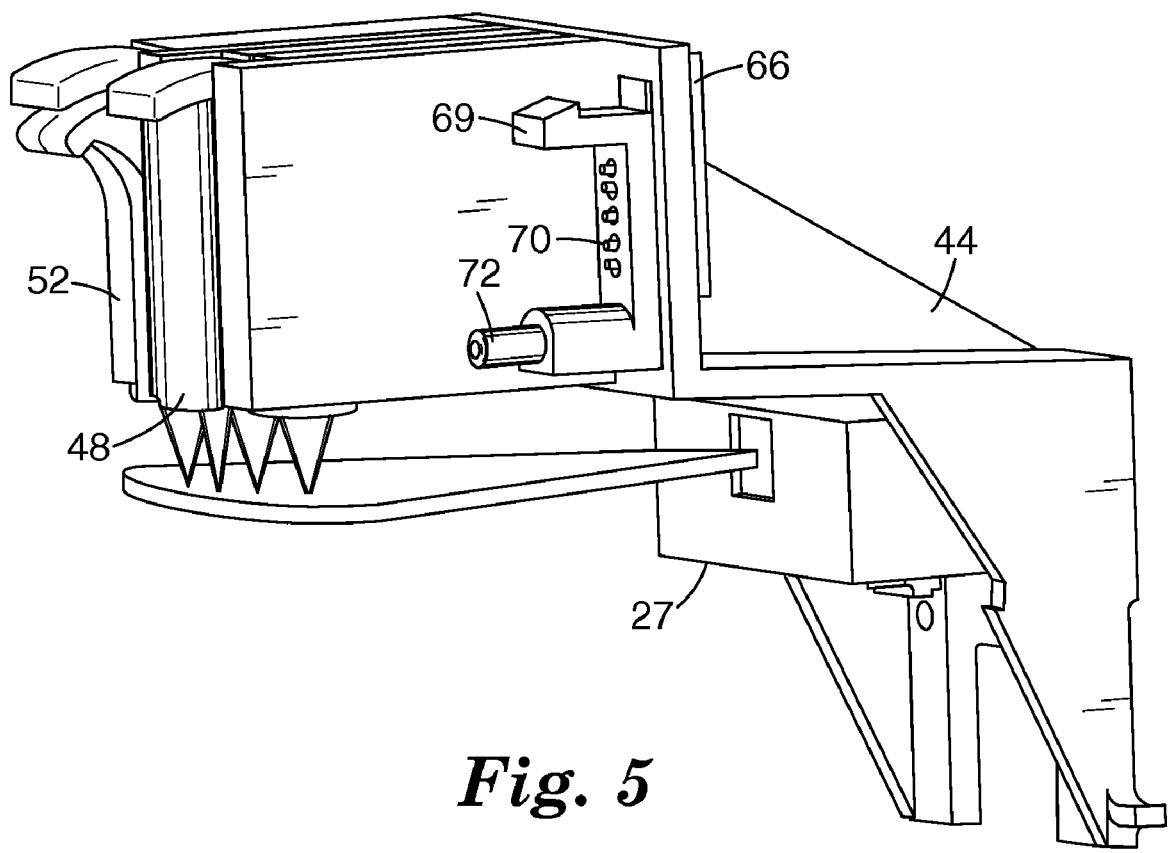
FIG. 5 is a perspective diagram illustrating a front side view of an exemplary set of removable optical modules having one module removed to expose a module connector.

FIG. 5 is perspective diagram illustrating a front side view of an exemplary set of removable optical modules having one module removed to expose a module connector. In particular, module housing 46 is not shown in FIG. 5, and optical module 56 has been removed to expose optical modules 52 and 48 along with the connections for removed module 56.

Release lever 58 (FIG. 3) of optical module 56 securely attaches to attachment post 69 mounted to base arm 44. In this example, attachment post 69 extends into optical module 56 and couples to release lever 58. In other embodiments, other attachment mechanisms may be used to fix optical module 56 to base arm 44, such as a screw or snap fixation device.

Base arm 44 provides two different operational connections within module housing 46 for receiving and engaging optical module 56, once inserted. In particular, base arm 44 provides electrical contact board 66, which includes electrical connections 70 for coupling to the electrical contacts (not shown) contained within optical module 56. Electrical connections 70 allow control unit 23 to communicate with electrical components within module 56. For example, module 56 may include electrical circuits, hardware, firmware, or any combination thereof. In one example, the internal electrical components may store and output to control unit 23 unique identification information, such as a serial number. Alternatively, or in addition, the electrical components may provide information describing the specific characteristics of the optical components contained within the removable module 56. For example, the electrical components may include programmable read-only memory (PROM), flash memory, or other internal or removable storage media. Other embodiments may include a set of resistors, a circuit or an imbedded processor for outputting a unique signature of optical modules 48, 52 or 56 to control unit 23. In another example, optical module 56 may include a laser source and other components that form part of a laser valve control system, i.e. laser valve control system 51.

Electrical contact board 66 may be removed and replaced with another version associated with a different removable optical module. This option may support upgrades in device capability. In other embodiments, connections 70 may contain more or less connection pins.

In addition, base arm 44 and module housing 46 provide optical channel 72 within the location for receiving optical module 56. Optical channel 72 is connected to fiber optic coupler 68 (FIG. 4) that interfaces with a leg of fiber optic bundle 14. Optical channel 72 inserts into a location within optical module 56. The light captured by optical module 56 may be directed through optical channel 72, fiber optic coupler 68 and fiber optic bundle 15 to the detector. Fittings between these connections may be tight to ensure that light does not escape or enter the optical path.

In some embodiments, the connections to optical module 56 may be arranged in a different configuration. For example, the connections may be located in another position for accepting optical module 56 from another direction. In other embodiments, electrical connections may be located on one side of optical module 56 while an optical connection is located on a second surface of module 56. In any case, the electrical and optical connections located within the location of module housing 46 accommodate a removable optical module, i.e., optical module 56 in this example.

The optical and electrical connections of module 56 described in FIG. 5 may be used with any module, including optical modules 48 and 52. In addition, the connections for each optical module may not be identical. Since connections may be modified for coupling with a desired removable optical module, the connections utilized by any particular optical module inserted within a particular location of module housing 46 may vary at any time.

Figure 6A:
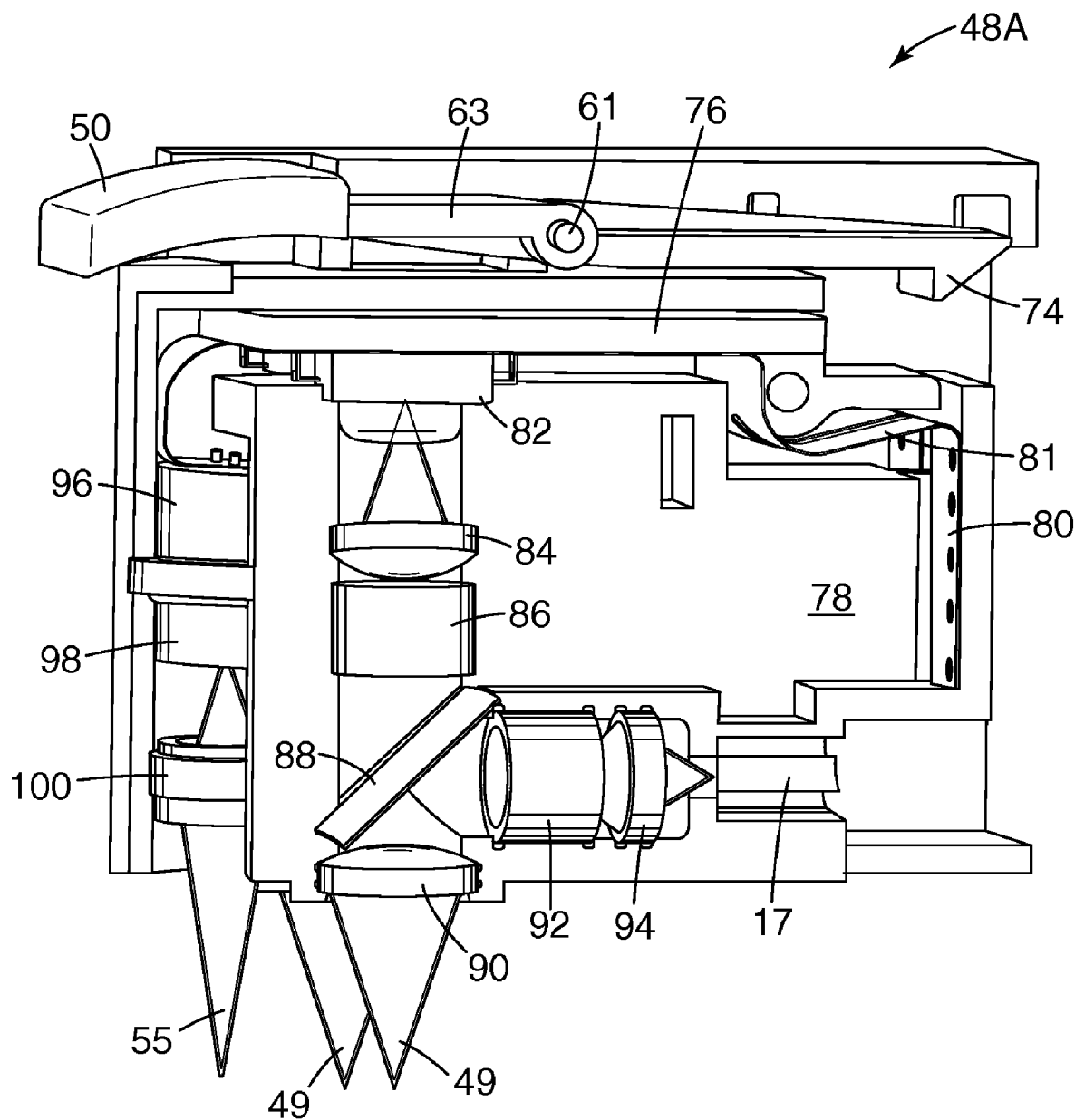
FIGS. 6A and 6B are perspective diagrams illustrating the components within exemplary main removable optical modules.

FIG. 6A is perspective diagram illustrating the components within an exemplary main removable optical module 48A. In the example of FIG. 6A, main optical module 48A includes release lever 50, pivot pin 51 and latch 74. Internal housing 78 separates each side of module 48A and contains electrical contacts pad 80 connected to ribbon 81. Optical components include LED 82, collimating lens 84, excitation filter 86, dichrotic filter 88, focusing lens 90, detection filter 92 and lens 94. Optical output port 17 couples to a leg of fiber optic bundle 14. A separate set of optical components for a second optical channel (not shown) are located on the other side of internal housing 78. In addition, main module 48A includes connector 96, laser diode 98 and focusing lens 100 as part of a laser valve control system 51 controlled by control unit 23.

Release lever 50 is attached to optical module 48A by a pivot pin 61. Pivot pin 61 allows release lever 50 to rotate about the axis of the pin. When release lever 50 is depressed, arm 63 rotates counter-clockwise to raise latch 74. Once latch 74 is raised, optical module 48A may be free for removal from module housing 46. There may be a spring or other mechanism maintaining a bias force against release lever 50 to maintain latch 74 in a down position. In some embodiments, a spring may be included around pivot pin 61 to provide a moment arm that keeps latch 74 in the down, or latched, position. In other embodiments, other mounting mechanisms may be added to or used in place of the described lever. For example, optical module 48A may be attached to module housing 46 by one or more screws or pins.

Mounting board 76 may be installed within optical module 48A for attaching communication ribbon 81 and LED 82. Ribbon 81 is connected to electrical contacts pad 80 and provides a connection between the pad and electrical components within optical module 48A. Contacts pad 80 and ribbon 81 may carry the information required for both sides of main optical module 48A, including the laser valve control system 51 and any internal memory or other storage medium. Ribbon 81 may be flexible for weaving within optical module 48A. Ribbon 81 may contain a plurality of electrically conductive wires to communicate signals between the electrical components and control unit 23 and/or to deliver power to the electrical components. In some embodiments, each electrical component may have a separate cable connecting the component with control unit 23. A technician may need to disconnect a cable or flex circuit from module housing 46 when removing optical module 48A from the housing.

In some embodiments, optical module 48A may contain a detector for detecting light from disk 13 and electronics for processing and storing the data. The electronics may contain a telemetry circuit for wirelessly transmitting data representing the detected light to control unit 23. Wireless communication may be performed by infrared light, radio frequency, Bluetooth, or other telemetry technique. Optical module 48A may also include a battery to power the electronics, which may be rechargeable by control unit 23.

LED 82 is affixed to mounting board 76 and electrically coupled to ribbon 81. LED 82 produces excitation light 49 of a predetermined wavelength to excite the sample 22. After light 49 leaves LED 82, the light is expanded by collimating lens 84 before the light enters excitation filter 86. The light 49 of one wavelength band is passed by dichrotic filter 88 and is focused on a sample by focusing lens 90. The light 49 excites the sample and fluorescence is collected by focusing lens 90 and delivered to detection filter 92 by dichrotic filter 88. The resulting wavelength band of light is collected by lens 94 and delivered to optical output port 17 where the collected fluorescent light enters a leg of fiber optic bundle 14 for conveyance to detector 18.

Internal housing 78 may support all components included in the excitation of the sample and detection of fluorescent light emitted by the sample for a selected wavelength. On the other side of internal housing 78, a similar configuration of optical components may be included to produce light of a different wavelength and detect the corresponding different fluorescent wavelength. Separation of each side may eliminate light contamination from one side entering the optical channel of the other side.

Housed partially between each side of module 48A may be the components of the laser valve control system 51, including connector 96, laser diode 98 and focusing lens 100. Internal housing 78 may provide physical support for these components. Ribbon 81 is connected to connector 96 for communicating drive signals and power to the laser source. Laser diode 98 is connected to connector 96 and produces the laser energy 55 used to open valves on disk 13. Laser diode 98 delivers this near-infrared (NIR) light to focusing lens 100 for directing the laser energy 55 to specific valves on disk 13. An NIR sensor may be located below disk 13 for locating particular valves that need to be opened. In other embodiments, these components may be housed separately from the optical components.

In some embodiments, emission lens 98 and focusing lens 100 of laser valve control system 51 may be contained within a single-channeled optical module, such as supplemental optical module 52 and 56 (FIG. 3).

Figure 6B:
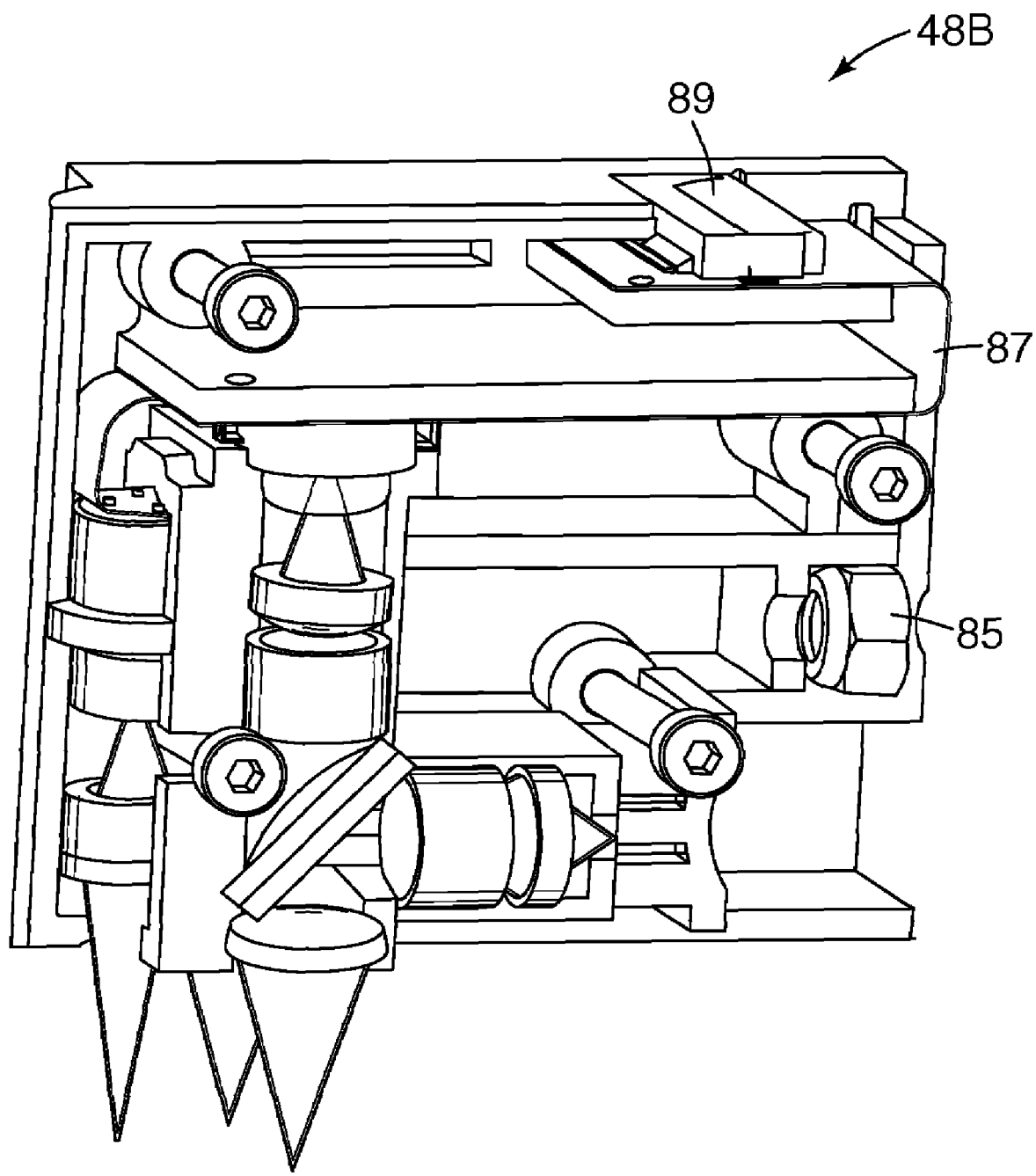

FIG. 6B is a perspective diagram illustrating the components within a different optical module substantially similar to FIG. 6A. Optical module 48B includes many of the same components as optical module 48A. Differences include nut 85, flex circuit 87 and flex circuit connector 89.

Optical module 48B does not require a latch mechanism for attaching to module housing 46. Alternatively, nut 85 is threaded and is engaged by a matching threaded bolt attached through module housing 46. Once tightened, optical module 48B is securely attached to detection device 10. In other embodiments, a different fastening device may be used. For example, a pin or track may lock optical module 48B into place.

Flex circuit 87 provides the electrical connection between components of optical module 48B with control unit 23. Flex circuit 87 is flexible to move between multiple locations. Flex circuit connector 89 is coupled to flex circuit 87 and provides a secure connection between optical module 48B. Flex circuit connector 89 must be disengaged to completely remove optical module 48B from module housing 46.

Figure 7A:
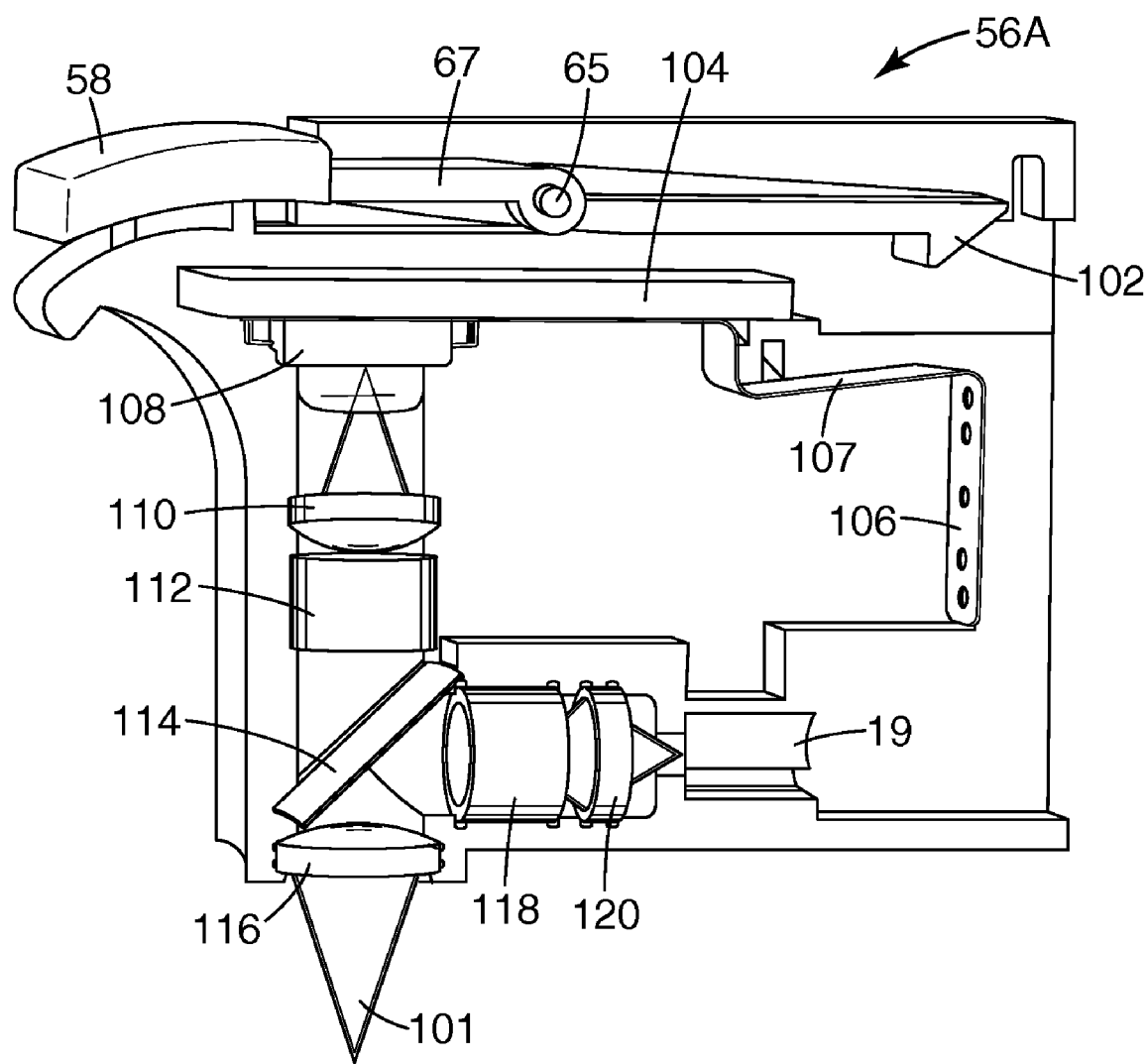
FIGS. 7A and 7B are perspective diagrams illustrating the components within exemplary supplemental removable optical modules.

FIG. 7A is a perspective diagram illustrating the components within an exemplary supplemental optical module that may be easily removed from or inserted into detection device 10. In the example of FIG. 7A, optical module 56A includes release lever 58, pivot pin 59 and latch 102, similar to main optical module 48A. Optical module 56A also includes electrical contacts pad 106 connected to ribbon 107. Ribbon 107 may also be connected to mounting board 104. Similar to main optical module 48A, optical components include LED 108, collimating lens 110, excitation filter 112, dichrotic filter 114, focusing lens 116, detection filter 118 and lens 120. Optical output port 19 couples to a leg of fiber optic bundle 14.

Release lever 58 is attached to optical module 56A by a pivot pin 65. Pivot pin 65 allows the release lever to rotate about the axis of the pin. When release lever 58 is depressed, arm 67 rotates counter-clockwise to raise latch 102. Once latch 102 is raised, optical module 56A may be free for removal from module housing 46. There may be a spring or other mechanism maintaining a bias force against release lever 58 to maintain latch 102 in a down position. Alternatively, a spring may be located above latch 102. In some embodiments, a spring may be included around pivot pin 65 to provide a moment arm that keeps latch 102 in the down, or latched, position. In other embodiments, other mounting mechanisms may be added to or used in place of the described lever. For example, optical module 56A may be attached to module housing 46 by one or more screws or pins.

Mounting board 104 may be installed within optical module 56A for attaching communication ribbon 107 and LED 108. Ribbon 107 is connected to electrical contacts pad 106 and provides a connection between the pad and electrical components within optical module 56A. Contacts pad 106 and ribbon 107 may carry the information required for operating the optical components. Ribbon 107 may be flexible for weaving within optical module 56A. Ribbon 107 may contain a plurality of electrically conductive wires to communicate signals between the components and control unit 23 and/or deliver power to the electrical components. In some embodiments, each electrical component may have a separate cable connecting the component with control unit 23. A technician may need to disconnect a cable or flex circuit from module housing 46 when removing optical module 56A from the housing.

In some embodiments, optical module 56A may contain a detector for detecting light from disk 13 and electronics for processing and storing the data. The electronics may contain a telemetry circuit for wirelessly transmitting data representing the detected light to control unit 23. Wireless communication may be performed by infrared light, radio frequency, Bluetooth, or other telemetry technique. Optical module 56A may also include a battery to power the electronics, which may be rechargeable by control unit 23.

LED 108 is affixed to mounting board 104 and electrically coupled to ribbon 107. LED 108 produces excitation light 101 of a predetermined wavelength to excite the sample 22. After light 101 leaves LED 108, the light is expanded by collimating lens 110 before the light enters excitation filter 112. The light 101 of one wavelength band is passed by dichrotic filter 114 and is focused on a sample by focusing lens 116. The light 101 excites the sample and fluorescence is collected by focusing lens 116 and delivered to detection filter 118 by dichrotic filter 114. The resulting wavelength band of light is collected by lens 120 and delivered to optical output port 19 where the collected fluorescent light enters a leg of fiber optic bundle 14 for conveyance to detector 18.

Supplemental optical module 56A may also contain the components of the laser valve control system 51. Laser valve control system 51 may be the only system used within device 10 or one of a plurality of laser valve control systems. The components used for this system may be similar to the components described in optical module 48A of FIG. 6A.

The components of supplemental optical module 56A may be similar to any supplemental optical module or any optical module used to emit and detect one wavelength band of light. In some embodiments, the components may be altered in configuration to accommodate different experimental applications. For example, any optical modules may be modified to be inserted from a different direction or to be placed within the device at a different position with respect to disk 13. In any case, the optical modules may be removable to provide modification flexibility to device 10.

Figure 7B:
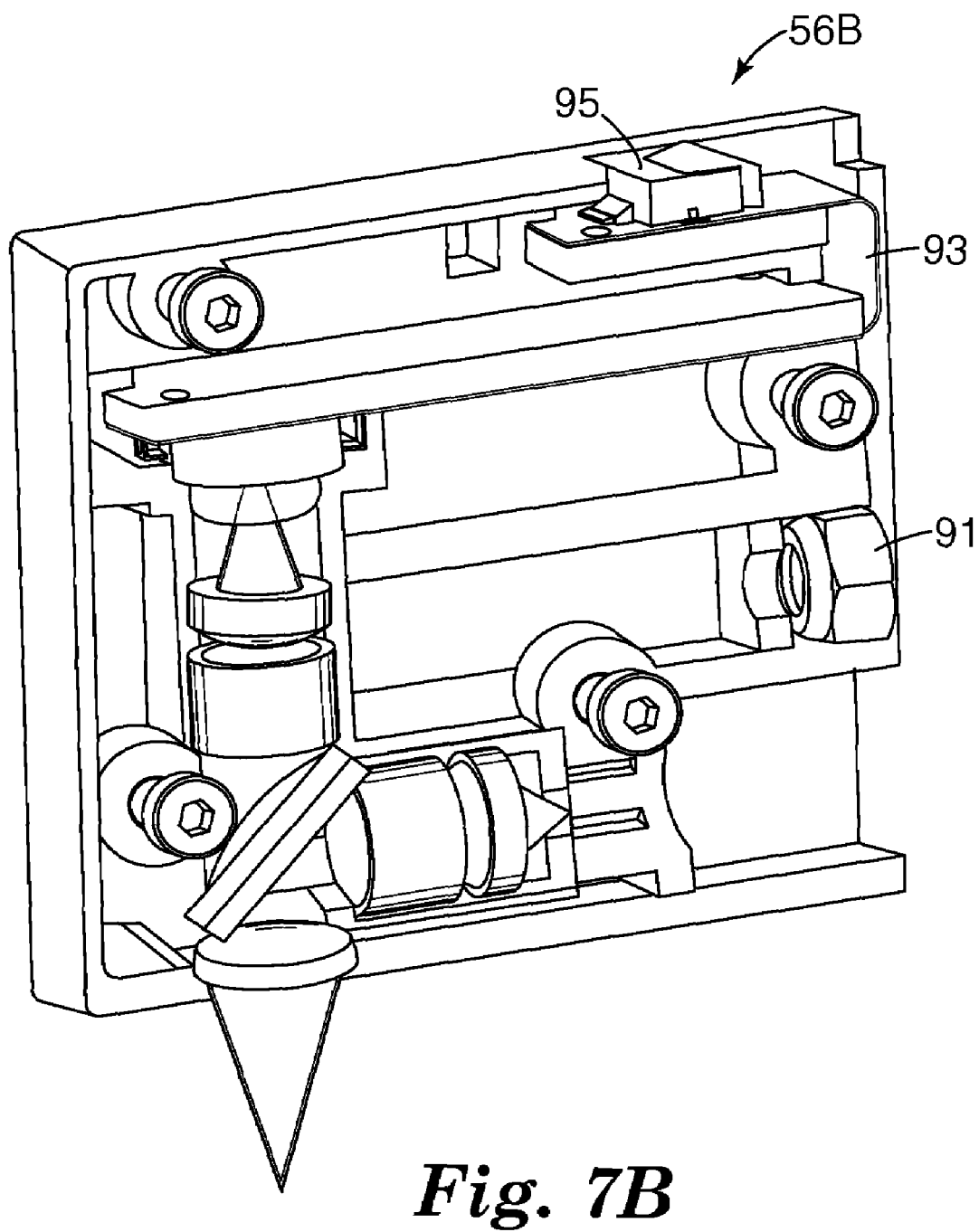

FIG. 7B is a perspective diagram illustrating the components within a different supplemental optical module substantially similar to FIG. 7A. Optical module 56B includes many of the same components as optical module 56A. Differences include nut 91, flex circuit 93 and flex circuit connector 95.

Optical module 56B does not require a latch mechanism for attaching to module housing 46. Alternatively, nut 91 is threaded and is engaged by a matching threaded bolt attached through module housing 46. Once tightened, optical module 56B is securely attached to detection device 10. In other embodiments, a different fastening device may be used. For example, a pin or track may lock optical module 56B into place.

Flex circuit 93 provides the electrical connection between components of optical module 56B with control unit 23. Flex circuit 93 is flexible to move between multiple locations. Flex circuit connector 95 is coupled to flex circuit 93 and provides a secure connection between optical module 56B. Flex circuit connector 95 must be disengaged to completely remove optical module 56B from module housing 46.

Figure 8:
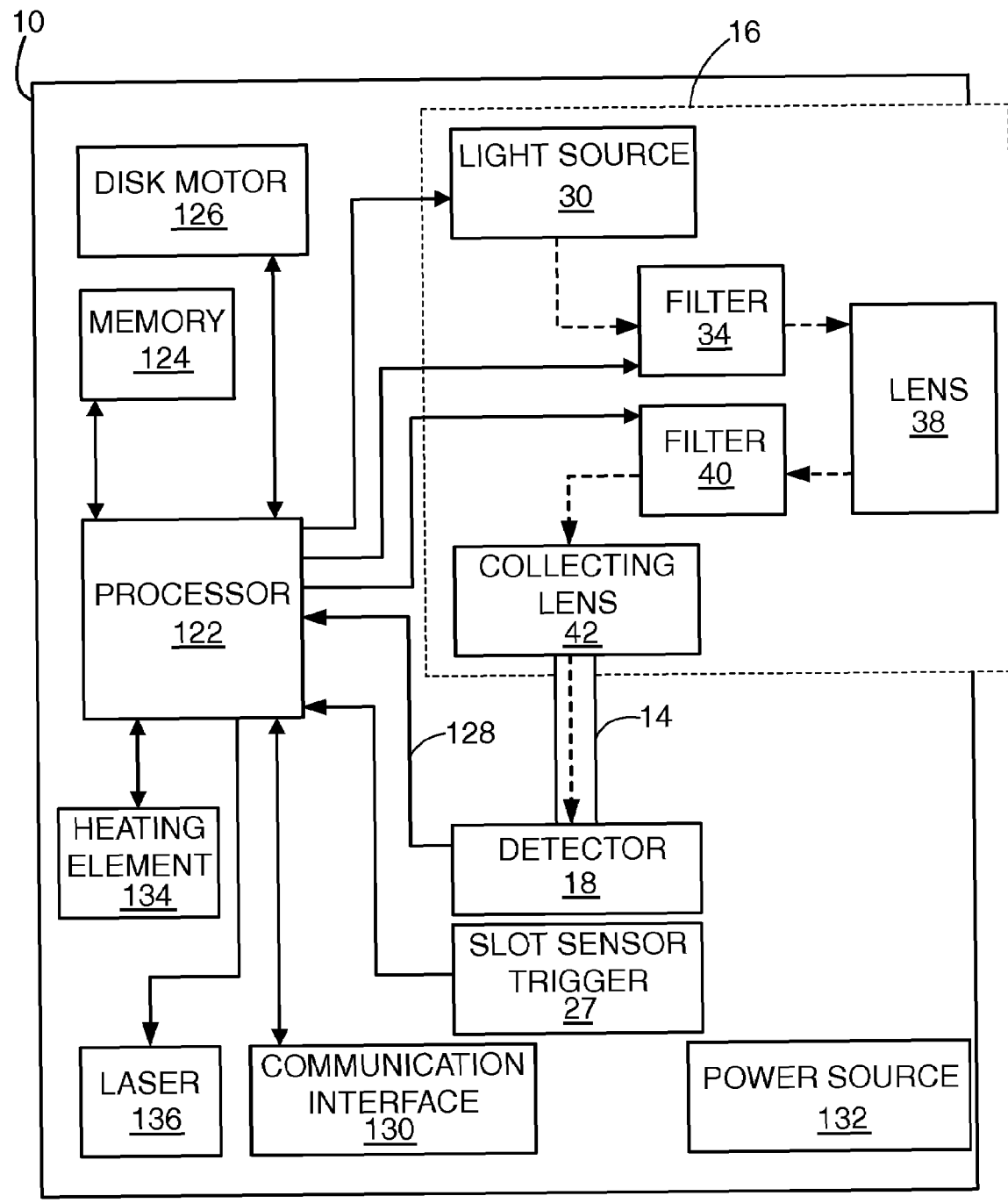
FIG. 8 is a block diagram illustrating an example embodiment of the multiplex fluorescence detection device in further detail.

FIG. 8 is a functional block diagram of the multiplex fluorescence detection device 10. In particular, FIG. 8 indicates the electrical connections between device components and the general paths of light through the components. In the example of FIG. 8, device 10 includes at least one processor 122 or other control logic, memory 124, disk motor 126, light source 30, excitation filter 34, lens 38, detection filter 40, collecting lens 42, detector 18, slot sensor trigger 27, communication interface 130, heating element 134, laser 136 and power source 132. As shown in FIG. 3, lens 38 and collecting lens 42 need not be electrically connected to another component. Further, light source 30, filters 34 and 40, lens 38 and collecting lens 42 are representative of one optical module 16. Although not illustrated in FIG. 8, device 10 may contain additional optical modules 16, as described previously. In that case, each additional optical module may include components arranged substantially similarly as to those shown in FIG. 8.

Light follows a certain path through several components in FIG. 8. Once light is emitted by light source 30, it enters excitation filter 34 and leaves as light of a discrete wavelength. It then passes through lens 38 where it leaves detection device 10 and excites sample 22 within a process chamber (not shown). Sample 22 responds by fluorescing at a different wavelength, at which time this fluorescent light enters lens 38 and is filtered by detection filter 40. Filter 40 removes background light of wavelengths outside of the desired fluorescence from sample 22. The remaining light is sent through collecting lens 42 and enters a leg of fiber optic bundle 14 before being detected by detector 18. Detector 18 subsequently amplifies the received light signal.

Processor 122, memory 124 and communication interface 130 may be part of control unit 23. Processor 122 controls disk motor 126 to rotate or spin disk 13 as needed to collect fluorescence information or move fluid through disk 13. Processor 122 may use disk position information received from slot sensor trigger 27 to identify the location of chambers on disk 13 during rotation and synchronize the acquisition of florescence data received from the disk.

Processor 122 may also control when the light source 30 within optical module 16 is powered on and off. In some embodiments, processor 122 controls excitation filter 34 and detection filter 40. Depending on the sample being illuminated, processor 122 may change the filter to allow a different wavelength of excitation light to reach the sample or a different wavelength of fluorescence to reach collecting lens 42. In some embodiments, one or both filters may be optimized for the light source 30 of the particular optical module 16 and not changeable by processor 122.

Collecting lens 42 is coupled to one leg of fiber bundle 14 that provides an optical path for the light from the collecting lens to detector 18. Processor 122 may control the operation of detector 18. While detector 18 may constantly be detecting all light, some embodiments many utilize other acquisition modes. Processor 122 may determine when detector 18 collects data and may programmatically set other configuration parameters of detector 18. In one embodiment, detector 18 is a photomultiplier tube that capture fluorescence information from light provided by collecting lens 42. In response, detector 18 produces an output signal 128 (e.g., an analog output signal) representative of the received light. Although not shown in FIG. 8, detector 18 may concurrently receive light from other optical modules 16 of device 10. In that case, output signal 128 electrically represents a combination of the optical input received by detector 18 from the various optical modules 16.

Processor 122 may also control data flow from device 10. Data such as sampled fluorescence from detector 18, temperature of the samples from heating element 134 and related sensors, and disk rotation information may be stored into memory 124 for analysis. Processor 122 may comprise any one or more of a microprocessor, digital signal processor (DSP), application specific integrated circuit (ASIC), field-programmable gate array (FPGA), or other digital logic circuitry. Moreover, processor 122 provides an operating environment for firmware, software, or combinations thereof, stored on a computer-readable medium, such as memory 124.

Memory 124 may include one or more memories for storing a variety of information. For example, one memory may contain specific configuration parameters, executable instructions, and one may contain collected data. Therefore, processor 122 may use data stored in memory 124 for controlling device operation and calibration. Memory 124 may include any one or more of a random access memory (RAM), read-only memory (ROM), electronically-erasable programmable ROM (EEPROM), flash memory, or the like.

Processor 122 may additionally control heating element 134. Based upon the instructions contained within memory 124, the heating element 134 may be selectively driven to control the temperature of one or more chambers according to desired heating profiles. Generally, heating element heats one radial section of disk 13 as the disk spins. Heating element 134 may comprise a halogen bulb and reflector for focusing heating energy on a specific area of disk 13. In other embodiments, heating element 134 may heat one or more chambers sequentially. This embodiment would require disk 13 to be stationary while a chamber is heated. In any embodiment, heating element 134 may be capable of turning on and off extremely quickly as needed.

Laser 136 is used to control valve opening which allows contents of a holding chamber to flow to another chamber on disk 13, e.g., a reaction well or process chamber. Processor 122 and supporting hardware drives laser 136 to selectively open specific valves contained with disk 13. Processor 122 may interact with a laser sensor underneath disk 13 for determining the position of the laser relative to the desired valve. When in position, processor 122 outputs signals to direct laser 136 to produce a burst of energy targeted at the valve. In some cases, the burst may last for approximately 0.5 seconds, while other embodiments may include opening times of shorter or greater duration. A laser energy and pulse duration may be controlled by processor 122 through communication with laser 136.

Processor 122 utilizes communication interface 130 to communicate with data acquisition system 21. The communication interface 130 may include a single method or combination of methods to transfer data. Some methods may include a universal serial bus (USB) port or IEEE 1394 port for hardwire connectivity with high data transfer rates. In some embodiments, a storage device may be directly attached to one of these ports for data storage for post processing. The data may be pre-processed by processor 122 and ready for viewing, or the raw data may need to be completely processed before analyzing can begin.

Communications with detection device 10 may also be accomplished by radio frequency (RF) communication or a local area network (LAN) connection. Moreover, connectivity may be achieved by direct connection or through a network access point, such as a hub or router, which may support wired or wireless communications. For example detection device 10 may transmit data on a certain RF frequency for reception by the target data acquisition device 21. Data acquisition device 21 may be a general purpose computer, a notebook computer, a handheld computing device, or an application-specific device. Further, multiple data acquisition devices may receive the data simultaneously. In other embodiments, the data acquisition device 21 may be included with detection device 10 as one integrated detection and acquisition system.

In addition, detection device 10 may be able to download updated software, firmware, and calibration data from a remote device over a network, such as the internet. Communication interface 130 may also enable processor 122 to monitor inventory report any failures. If operational problems occur, processor 122 may be able to output error information to assist a user in trouble shooting the problems by providing operational data. For example, processor 122 may provide information to help the user diagnose a failing heating element or a synchronization problem.

Power source 132 delivers operating power to the components of device 10. Power source 132 may utilize electricity from a standard 115 Volt electrical outlet or include a battery and a power generation circuit to produce the operating power. In some embodiments, the battery may be rechargeable to allow extended operation. For example, device 10 may be portable to detection of biological samples in an emergency, such as a disaster area. Recharging may be accomplished through the 115 Volt electrical outlet. In other embodiments, traditional batteries may be used.

Figure 9:
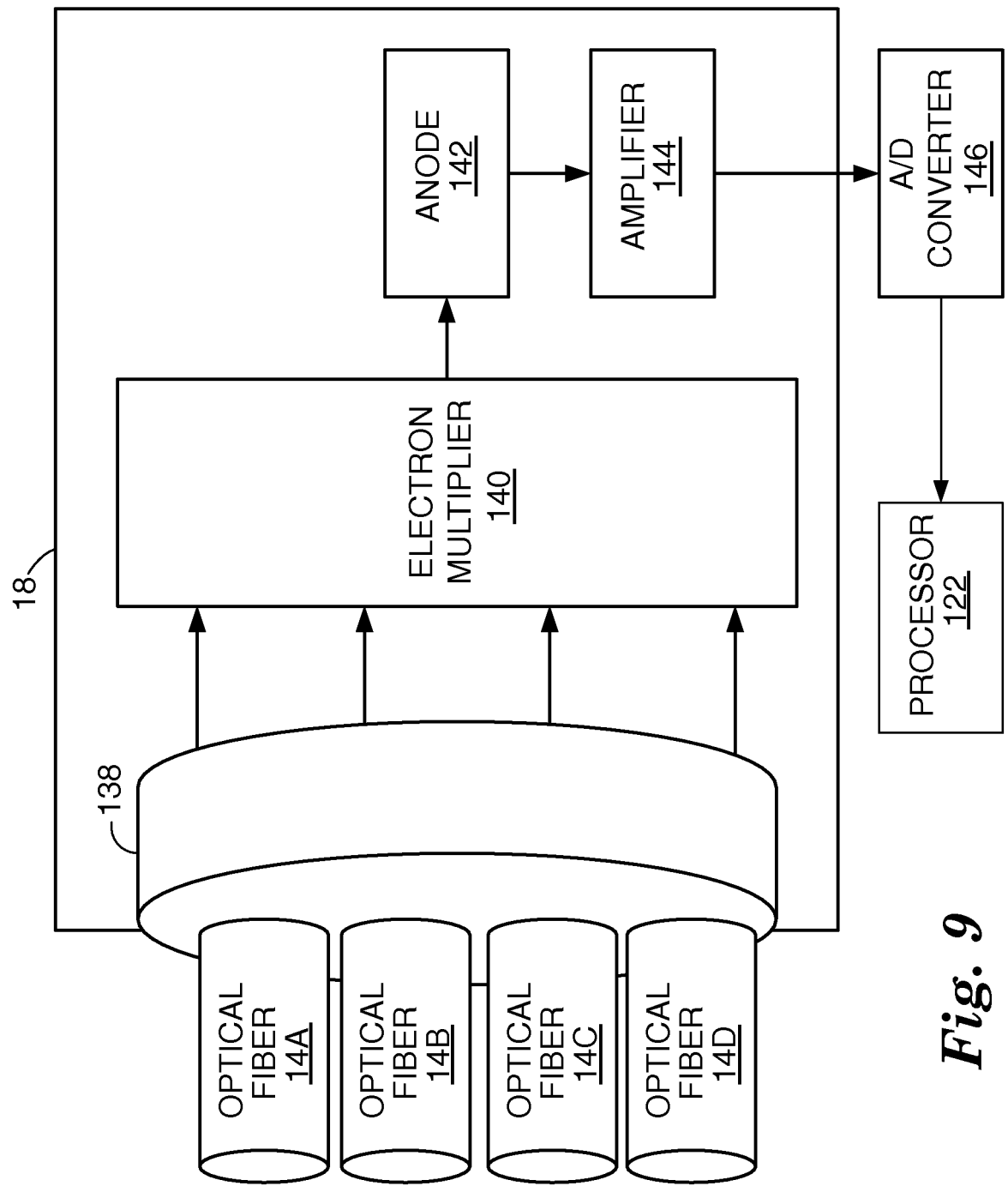
FIG. 9 is a block diagram of the a single detector coupled to four optical fibers of the optical fiber bundle.

FIG. 9 is a functional block diagram of the single detector 18 coupled to four optical fibers of the optical fiber bundle. In this embodiment, detector 18 is a photomultiplier tube. Each leg of fiber optic bundle 14, optical fiber 14A, optical fiber 14B, optical fiber 14C and optical fiber 14D, couples to an optical input interface 138 of detector 18. In this manner, light carried by any of optical fibers 14 is provided to a single optical input interface 138 of detector 18. The optical input interface 138 provides the aggregate light to electron multiplier 140. Anode 142 collects the electrons and produces a corresponding analog signal as output signal.

In other words, as shown, the optical fibers 14 fit within the input optical aperture for detector 18. Consequently, detector 18 may be used to detect light from each leg of optic bundle 14 simultaneously. Optical input interface 138 provides the light to electron multiplier 140. For a photomultiplier tube, the photons from the optical fibers first hit a photoemissive cathode, which in turn releases photoelectrons. The photoelectrons then cascade by hitting a series of dynodes, more photoelectrons being emitted upon contact with each dynode. The resulting group of electrons have essentially multiplied the small light signals originally transmitted by the optical fibers 14. The increased number of electrons finally are collected by anode 142. This current from anode 142 is transferred by a current to voltage amplifier 144 as an analog output signal which is representative of the optical florescent signals from the sample provided by the plurality of optical modules 16.

Control unit 23 includes an analog to digital (A/D) converter 146 converts the analog signal to a stream of sampled digital data, i.e., a digital signal. Processor 122 receives the digital signal and stores the sampled data in memory 124 for communication to data acquisition device 21, as described in above. In some embodiments, A/D converter 146 may be contained within detector 18 instead of control unit 23.

In this manner, a single detector 18 may be utilized to collect all light from the optic bundle 14 and produce a signal representative thereof. Once the signal is amplified by amplifier 144 and converted to a digital signal, it may be digitally separated into data corresponding to the light collected by each individual optical modules 16. The entire (i.e., aggregate) signal may be separated by frequency range into each detected signal representative of each fluorescence. These frequencies may be separated by a digital filter applied by data acquisition device 21 or within device 10.

In other embodiments, the amplified signal may be separated by frequency using analog filters and sent to separate channels before A/D converter 146. Each channel may then be separately digitized and sent to the data acquisition device. In either case, the single detector is able to capture all florescence information from each optical module 16. Data acquisition device 21 may then plot and analyze the signal acquired from each chamber of disk 13 in real-time without the need for multiple detectors.

In some embodiments, detector 18 may not be a photomultiplier tube. In general, detector 18 may be any type of analog or digital detection device capable of capturing light from multiple legs of an optical delivery mechanism, i.e., fiber bundle 14, and producing a transmittable representation of the captured light.

Figure 10:
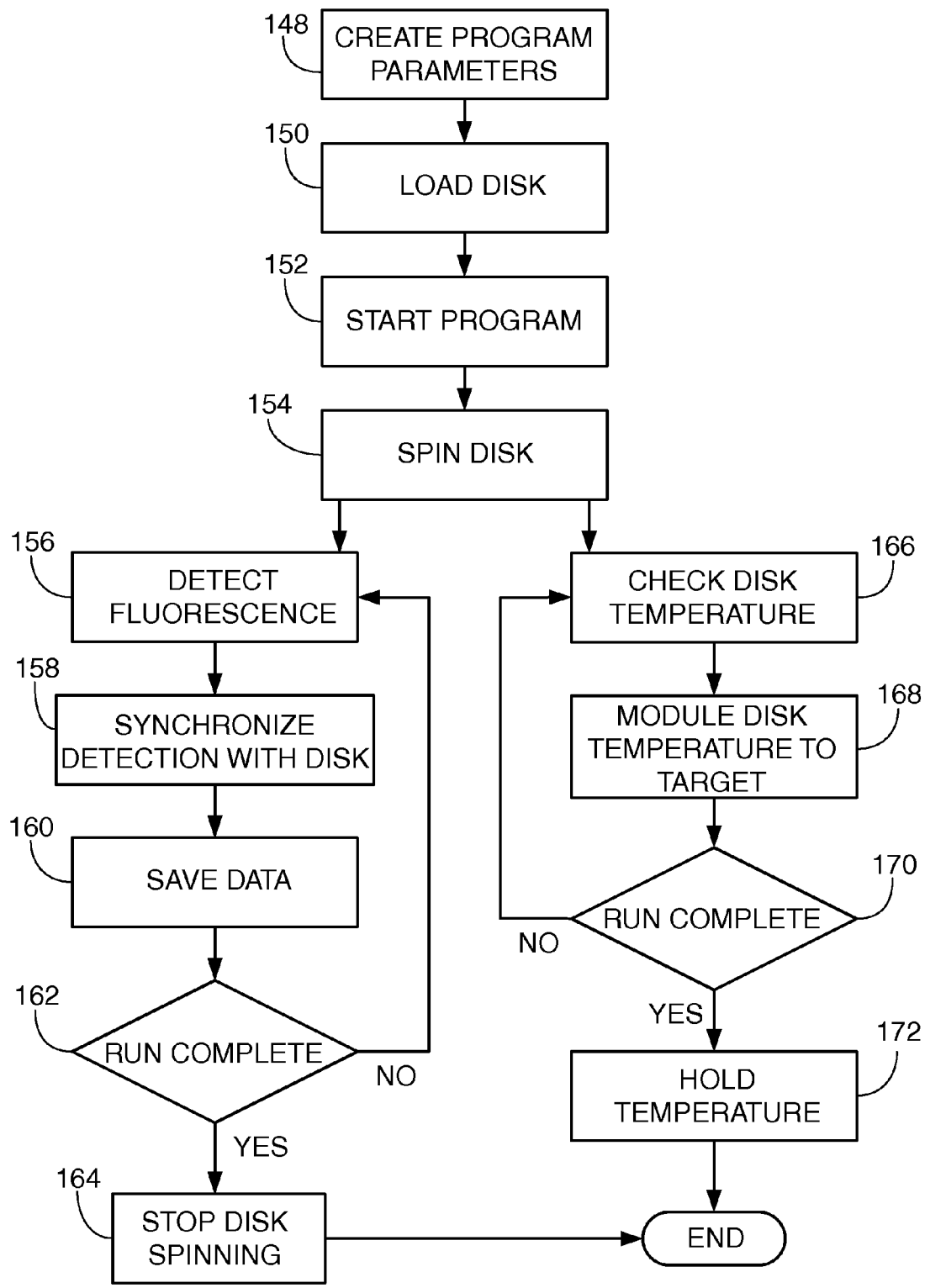
FIG. 10 is a flow diagram illustrating exemplary operation of the multiplex fluorescence detection device.

FIG. 10 is a flow diagram illustrating the operation of the multiplex fluorescence detection device 10. Initially, a user specifies program parameters on the data acquisition device 21 or via an interface with control unit 23 (148). For example, these parameters may include a velocity and time period for rotating disk 13, define temperature profiles for the reaction, and sample locations on disk 13.

Next, the user loads disk 13 into the detection device 10 (150). Upon securing the device 10, the user starts the program (152), causing control unit 23 to begin spinning the disk (154) at the specified rate. After the disk has begun to spin, two concurrent processes may occur.

First, the detection device 10 starts to detect fluorescence from the excitation light (156) produced by one or more reactions within one or more samples. The detector 18 amplifies the fluorescence signals from each sample, which are synchronized to each respective sample and time at which the fluorescence was emitted (158). During this process, processor 122 saves the captured data to memory 124 and may communicate the data to data acquisition device 10 in real-time to monitor the progress of the run and for additional processing (160). Alternatively, processor 122 may save the data within device 10 until the program is complete. The processor 122 continues to detect florescence of the samples and save data until the program is complete (162). Once the run is complete, control unit 23 stops the disk from spinning (164).

During this process, control unit 23 monitors the disk temperature (166) and modulates the disk, or each sample, temperature to attain the target temperature for that time (168). The control unit 23 continues to monitor and control the temperatures until the program is complete (170). Once the run is complete, control unit 23 holds the temperature of the samples to a target storage temperature, usually 4 degrees Celsius (172).

The operation of device 10 may vary from the example of FIG. 10. For example, the disk revolutions per minute may be modified throughout the program, and laser 136 may be utilized to open valves between chambers on the disk to allow for multiple reactions. These steps may occur in any order within the operation, depending on the program the user defines.

Figure 11:
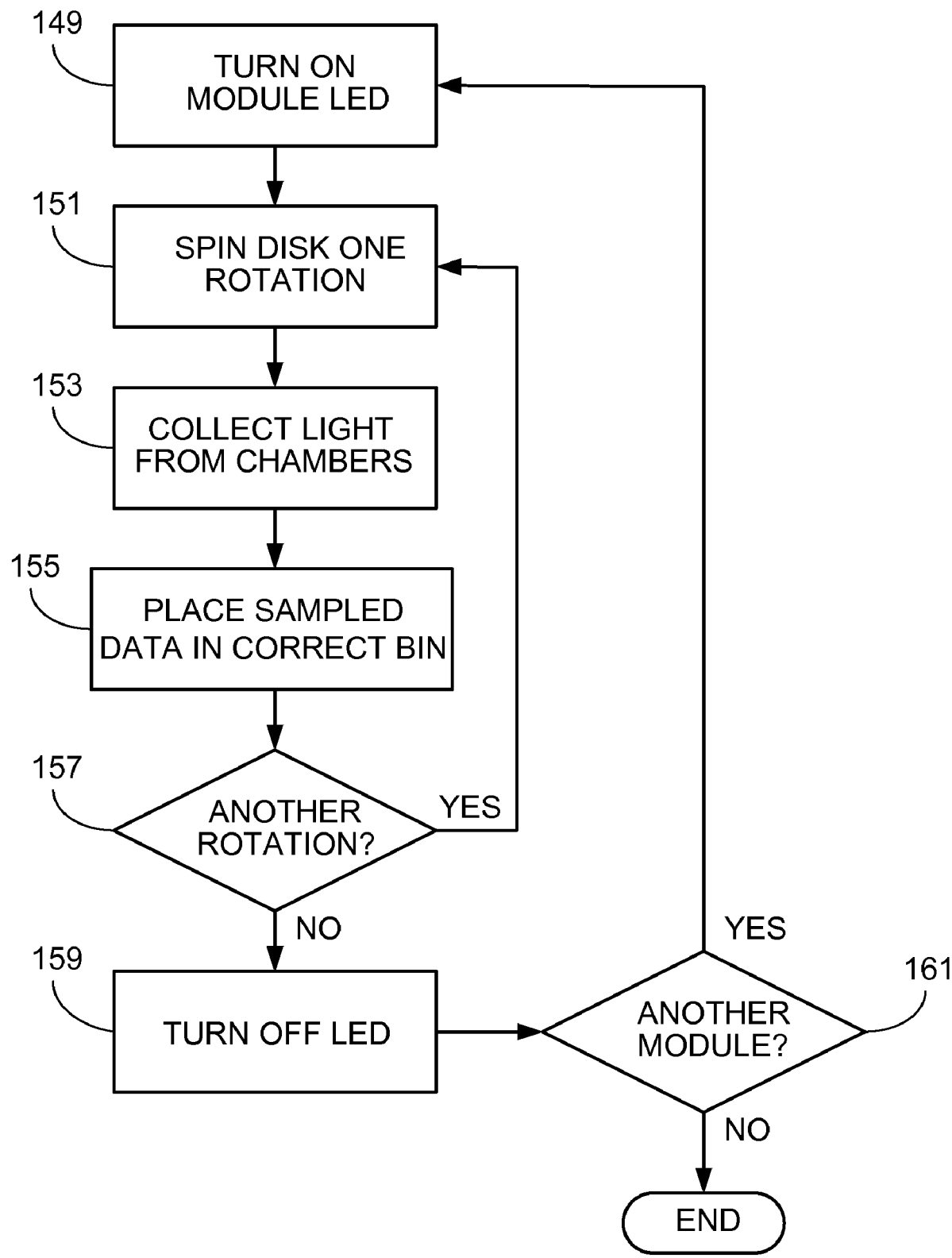
FIG. 11 is a flow diagram illustrating an exemplary method if detecting light and sampling data from the disk.

FIG. 11 is a flow diagram illustrating an exemplary method if detecting light and sampling data from the disk. Initially, a user specifies which modules will detect fluorescence from disk 13, and control unit 23 turns on the LED of a module (149). Once the LED has warmed to steady state, control unit 23 spins disk 13 one rotation at the rate of approximately 1470 revolutions per minute (151). During that rotation, the module collects light fluoresced from the process chambers of disk 13 (153), and control unit 23 places 16 samples from each process chamber in the memory BIN associated with each process chamber (155).

If disk 13 must be spun another rotation (157), control unit 23 executes another revolution of disk 13 (151). If 16 revolutions have been sampled, the module has completed detection with the LED. Therefore, each process chamber was sampled a total of 256 times and data acquisition device 21 integrates the samples to create a histogram of each process chamber. Control unit 23 turns the LED off (159). If another module must to used to continue detection (161), control unit 23 turns on the next module LED (149). If no other modules are needed to collect data, control unit 23 discontinues the collection of data from disk 13.

In some embodiments, each process chamber may be sampled more or less times. Control unit 23 may spin disk 13 at a faster rate to provide quicker results or spin disk 13 slower to acquire more samples. In other embodiments, LEDs from two or more modules may be turned on to detect fluorescence simultaneously in multiple wavelengths.

EXAMPLE

Figure 12:
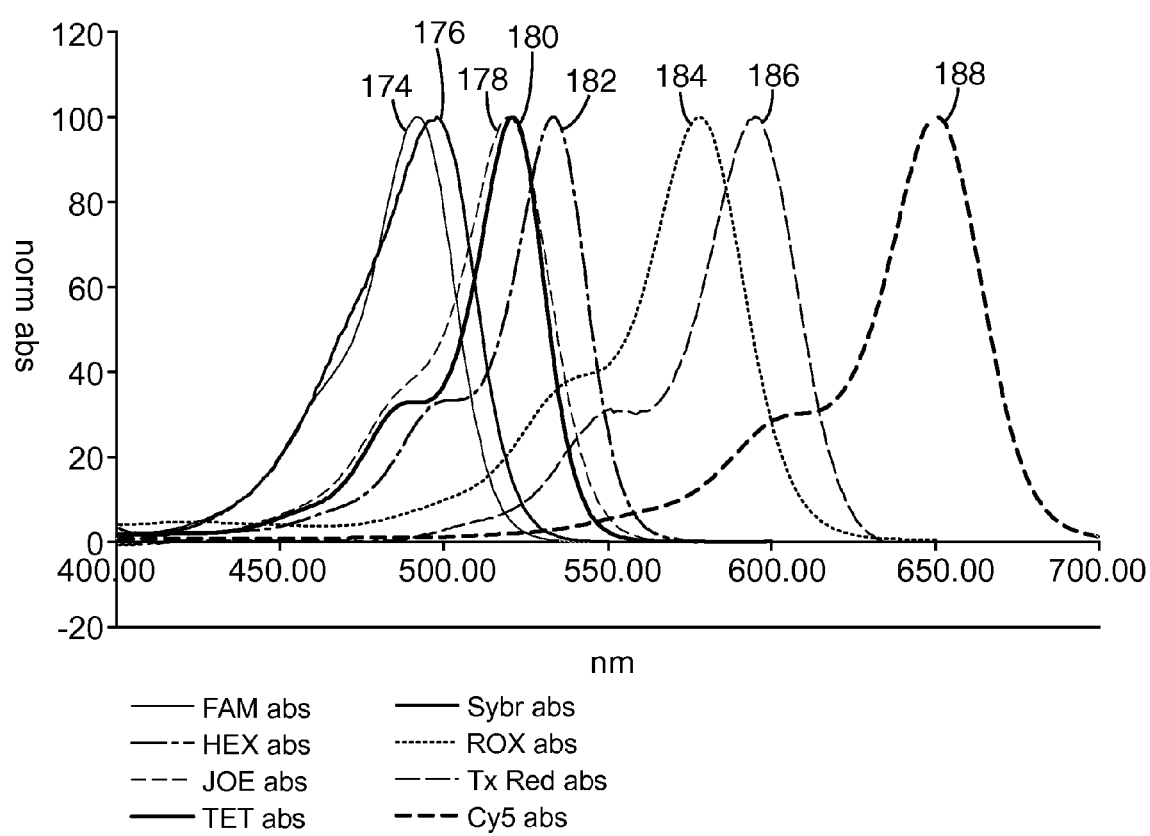
FIGS. 12 and 13 show the absorption and emission spectra of commonly used fluorescent dyes that may be utilized for multiplex PCR.
Figure 13:
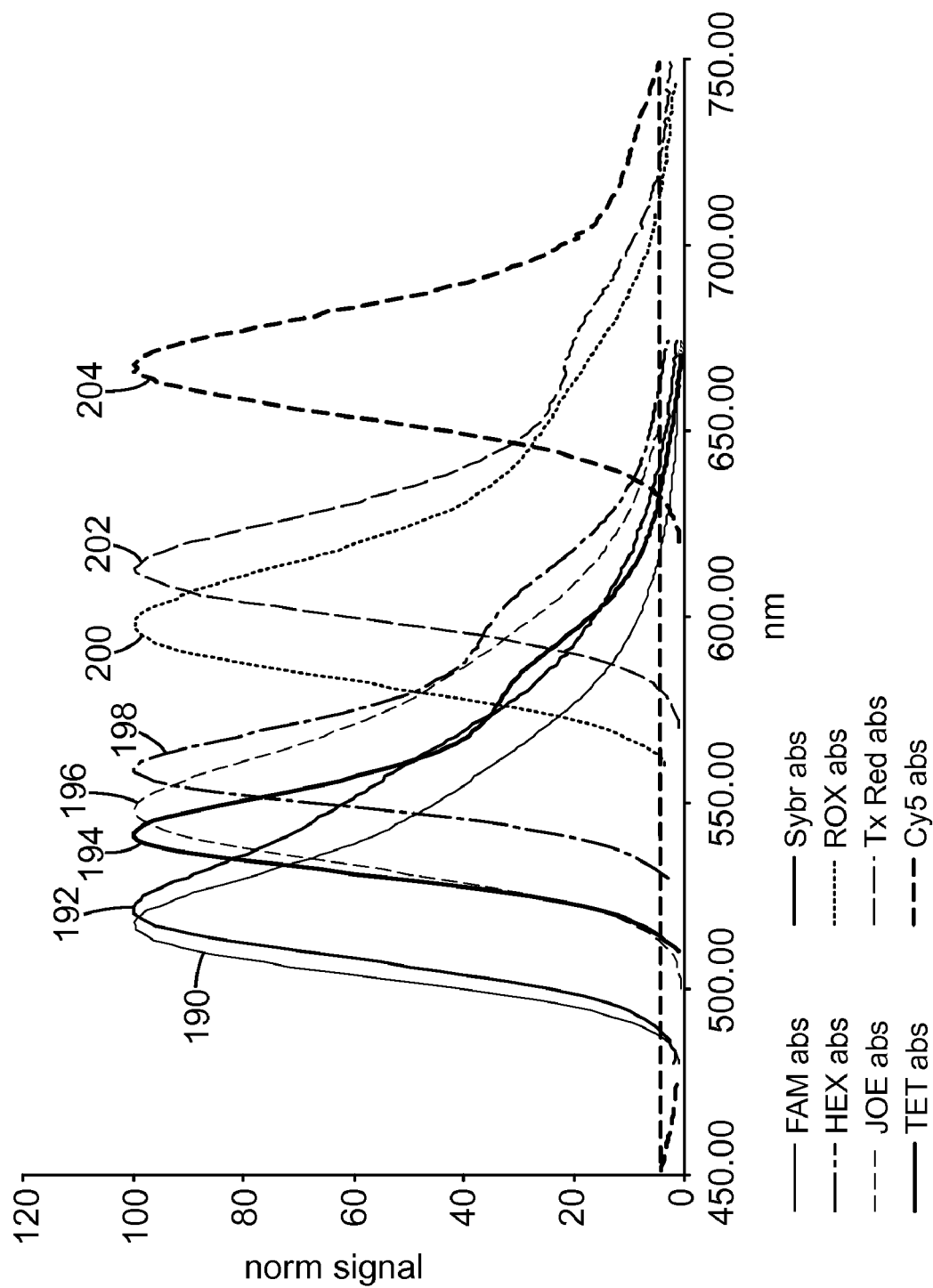

FIGS. 12 and 13 show the absorption and emission spectra of commonly used fluorescent dyes that may be utilized with device 10 for multiplex PCR. In these examples, the absorption maxima of the dyes vary from 480-620 nm, and the resulting emission maxima vary from 520-670 nm. The signals for each dye in FIG. 12 are numbered as FAM 174, Sybr 176, JOE 178, TET 180, HEX 182, ROX 184, Tx Red 186, and Cy5 188. The signals in FIG. 13 are FAM 190, Sybr 192, TET 194, JOE 196, HEX 198, ROX 200, Tx Red 202, and Cy5 204. FAM, HEX, JOE, VIC, TET, ROX are trademarks of Applera, Norwalk, Calif. Tamra is a trademark of AnaSpec, San Jose, Calif. Texas Red is a trademark of Molecular Probes. Cy 5 is a trademark of Amersham, Buckinghamshire, United Kingdom.

In one example, a 96 chamber disk was filled with different concentrations of FAM and ROX dye diluted in standard PCR reaction buffer. Four replicates of each dye were added in a 2× dilution series, starting from 200 nM FAM and 2000 nM ROX. Each sample volume was 10 µL. Chamber 82 had a mixture of 5 µL of 200 nM FAM and 5 µL of 2000 nM ROX. Device 10 was constructed as a two-channel multiplex PCR detection device having two optical modules 16 for detection of the dyes.

The first optical module (the FAM module) contained a blue LED, 475 nm excitation filter and a 520 nm detection filter. The second optical module (the ROX module) contained a green LED with a 560 nm excitation filter and a 610 nm detection filter. Another option would be to incorporate an orange LED and an excitation filter at 580 nm to optimize for ROX detection.

A PCR analysis was conducted, and fluorescent signals from the samples were multiplexed into a bifurcated fiber optic bundle. The fiber bundle was interfaced with a single detector, specifically a photomultiplier tube (PMT). Data was collected by a National Instruments data acquisition (DAQ) board interfaced with a Visual Basic data acquisition program executing on a general-purpose computer. Data was acquired while the disk was spinning at 1000 revolutions per minute (nominally). The FAM module and the ROX module were sequentially used to interrogate the samples. Each scan consisted of an average of 50 rotations. The raw data from the two optical modules is shown in FIGS. 14A and 14B.

Figure 14A:
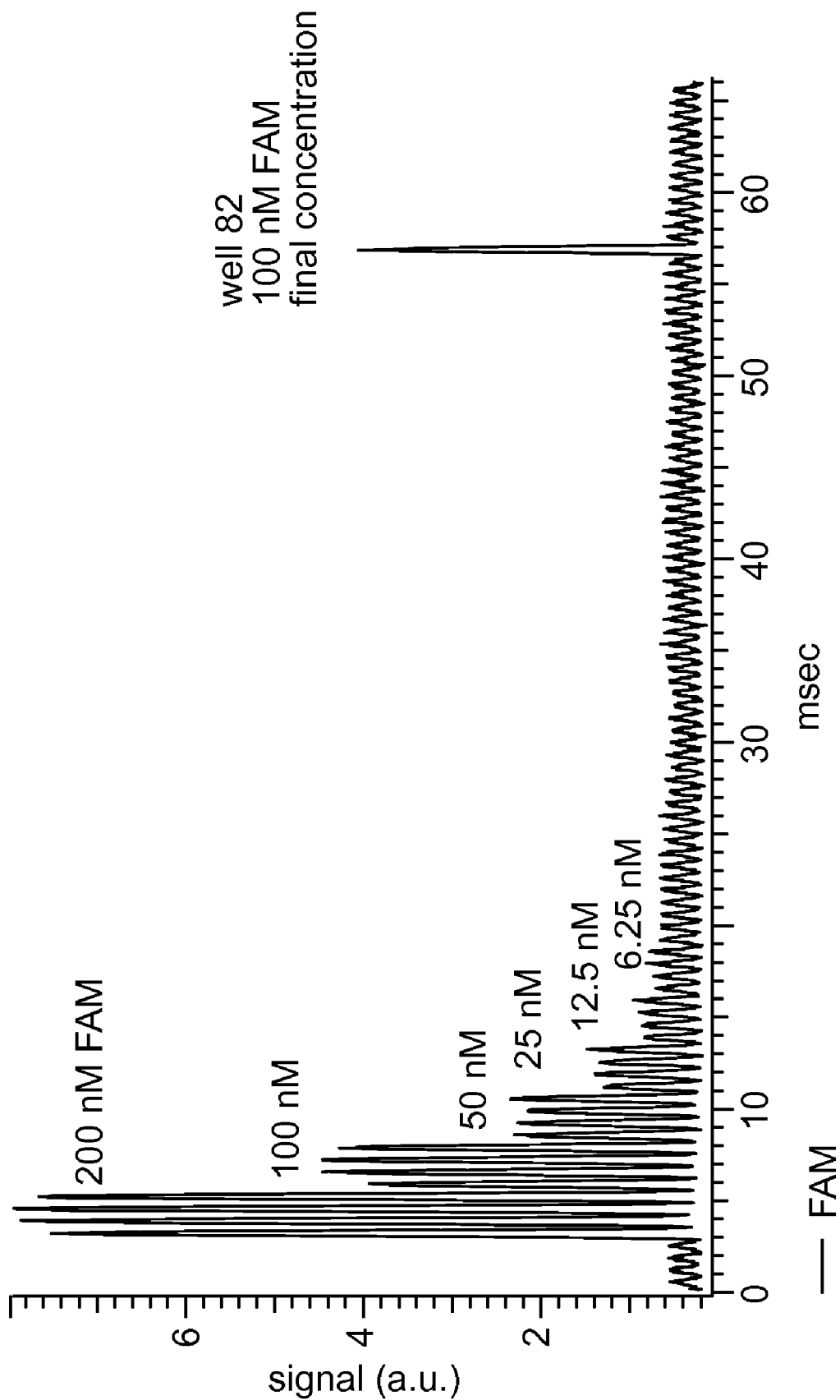
FIGS. 14A and 14B illustrate raw data acquired from two exemplary detection modules with a single detector during a PCR analysis.
Figure 14B:
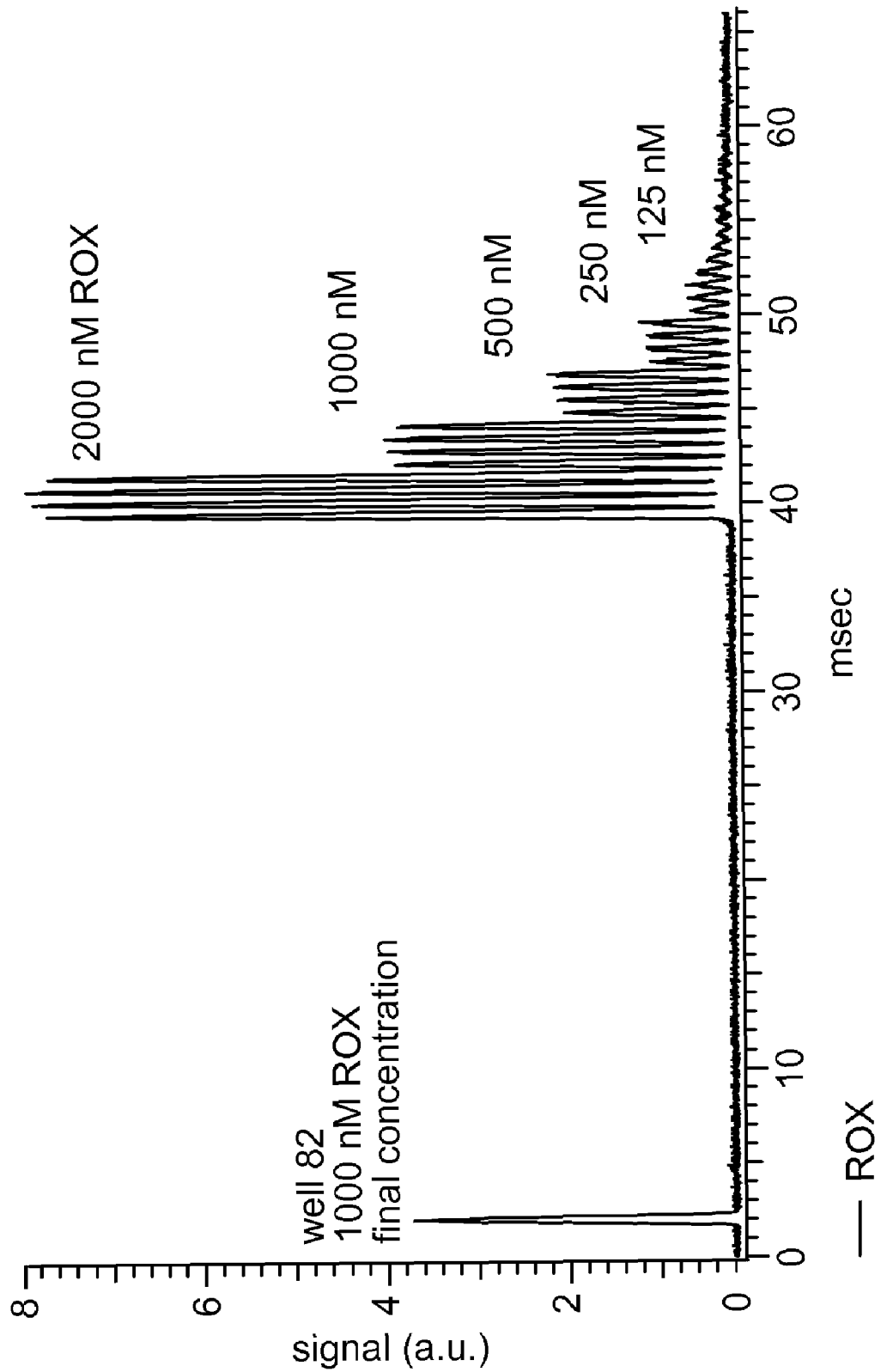

The graph in FIG. 14A was acquired by powering the LED in the FAM module, and the graph in FIG. 14B was acquired by powering the LED in the ROX module.

During the analysis, the collected data clearly showed that there was a time offset associated with optical modules being physically located over different chambers at any one time. An offset value was calculated by determining the time offset between optical modules 1 and 2 for a particular chamber, i.e., chamber 82 in this case. In other words, the time offset indicates the amount of time delay between data captured by the FAM module and data captured by the ROX module for the same chamber.

Figure 15:
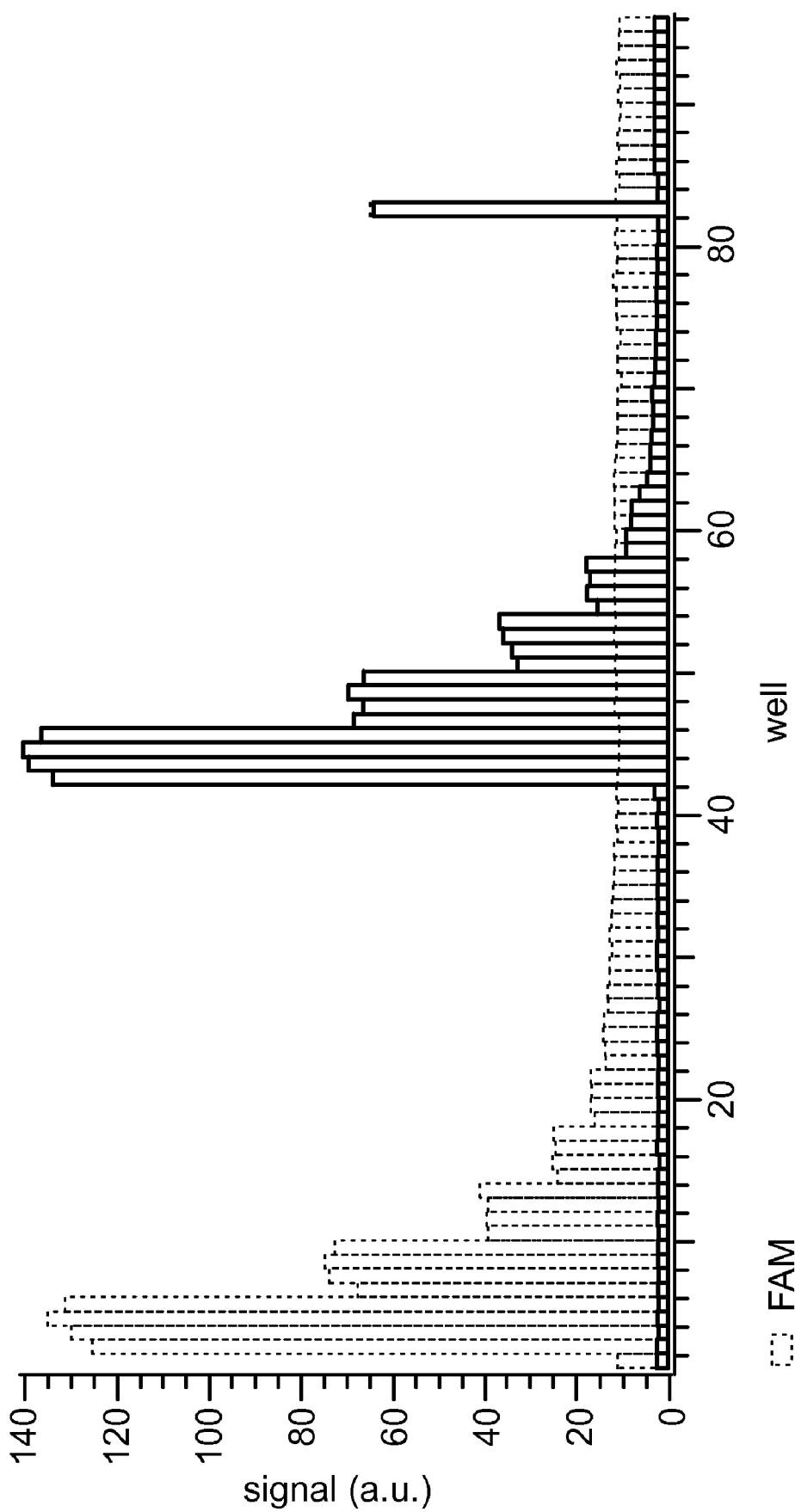
FIG. 15 is a graph that shows the data once adjusted for a time offset.

FIG. 15 is a graph that shows the offset-subtracted integrated data for each chamber. FAM is indicated by dotted line bars, ROX is indicated by solid line bars, and the ROX data is placed over the FAM data. The data showed that there was no signal from the ROX dye on optical module 1 and no signal from the FAM dye on optical module 2. There was a higher background on optical module 1, which may be rectified by using an optimized set of filters. The data was analyzed to determine the limit of detection (LOD), described as the signal equivalent to the baseline noise level. The baseline noise level was defined as the average of ten scans of a blank chamber plus 3 times the standard deviation.

Figure 16B:
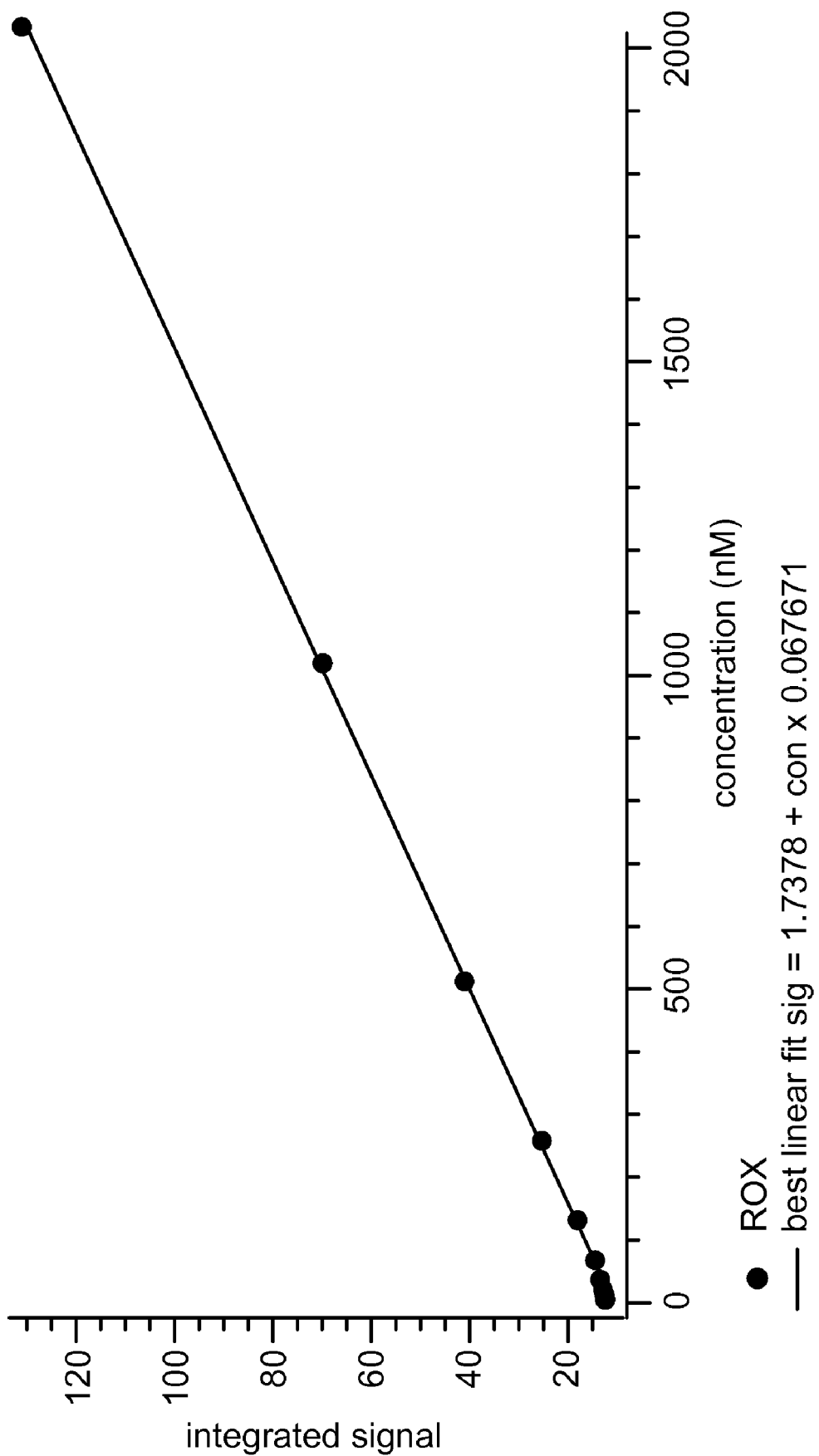

The LOD was determined by a linear least squares fit of the integrated signal plotted against the concentration of the FAM and ROX standards. The LOD of the FAM and ROX modules were calculated to be 1 and 4 nM, respectively, as shown in FIGS. 16A and 16B.

Figure 17:
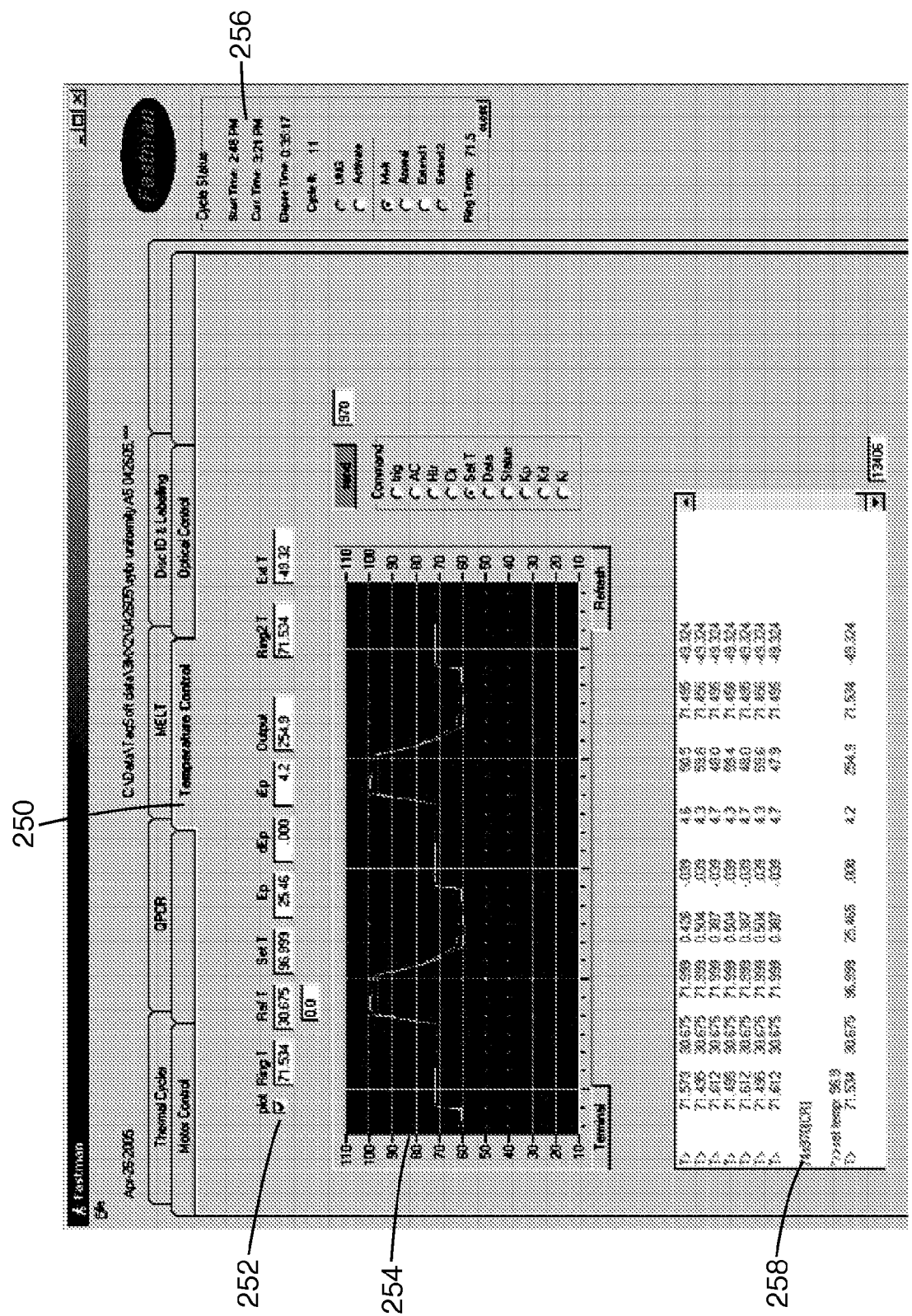
FIG. 17 is an exemplary screen shot of a temperature control user interface.

FIG. 17 is an exemplary screen shot of a temperature control user interface. Temperature control screen 250 is highlighted and shows temperature controls 252. Temperature graph 254 outputs temperature readings while status indicator 256 displays general information. Message window 258 displays commands when running detection device 10.

The technician may select temperature control screen 250 to view temperature information from device 10. Temperature control screen 250 is one of several screens which may be selected to display information associated with the operation of control unit 23 or data acquisition device 21. Screen 250 includes temperature controls 252 which display numerical information to the technician. Temperature graph 254 displays graphical temperature information as a graph of temperature as a function of time. In some embodiments, the technician may manually change the values located within temperature controls 252.

Status indicator 256 is always visible to the technician. Status indicator 256 displays relevant operational times, cycle number, temperature and other important information. Message window 258 displays current commands to control unit 23. Window 258 includes a scroll bar for locating any command delivered to control unit 23 during device 10 operation. In some embodiments, message window 258 may display error information or other important information to the technician.

Figure 18:
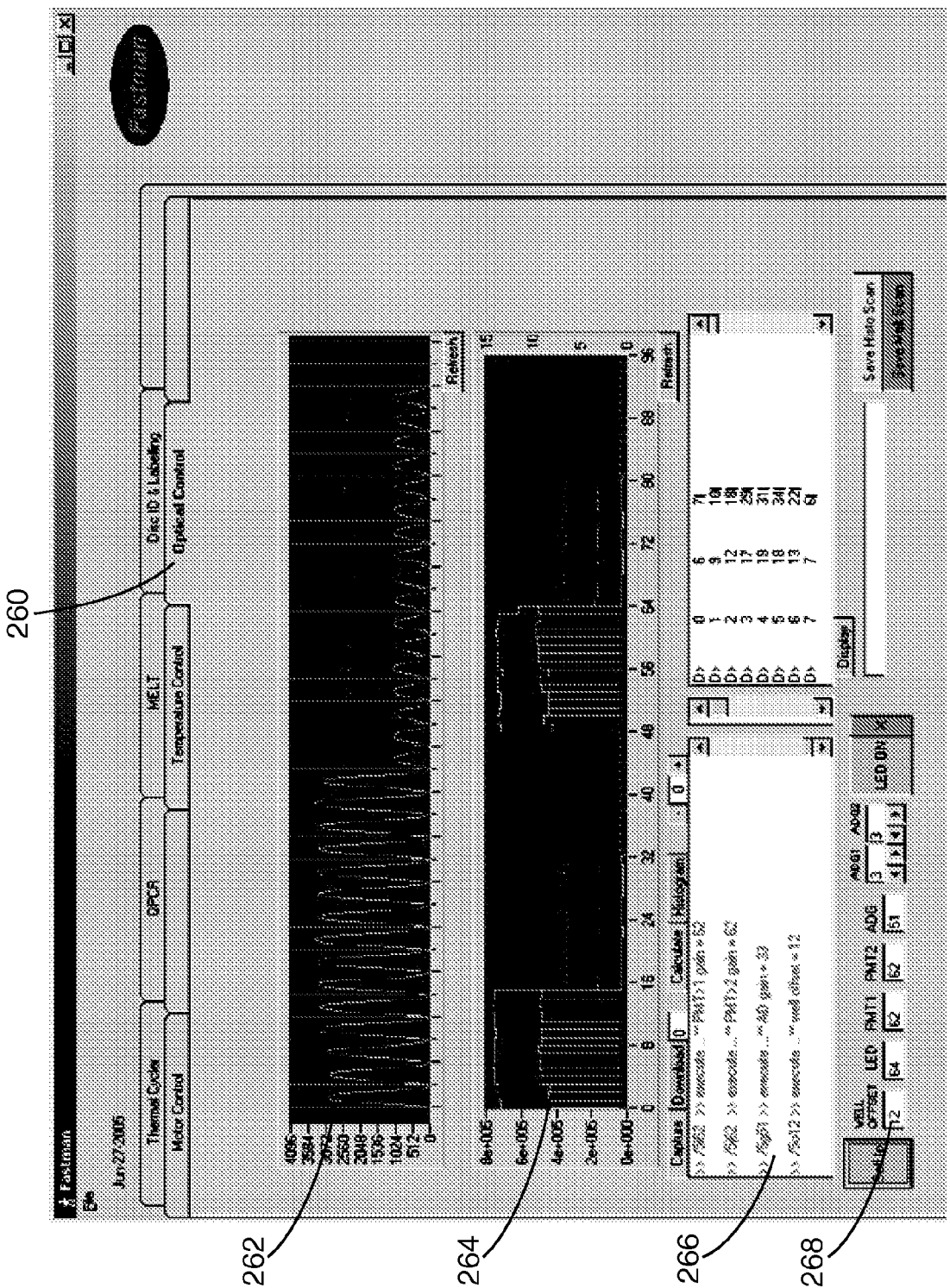
FIG. 18 is an exemplary screen shot of an optical control user interface.

FIG. 18 is an exemplary screen shot of an optical control user interface. Optical control screen 260 is highlighted and shows signal graph 262. Histogram 264 shows the integrated signal of each process chamber. Screen 260 also includes message window 266 and offset control 268.

Signal graph 262 displays the raw optical data detected by detection device 10. The signal displayed on graph 262 is the raw signal from optical modules 48, 52 and 56 and includes cycles that correspond to the signal change between process chambers. The technician may change offset control 268 to match the binning of signal into appropriate bins representing each process chamber with the signal waveform. The loss of signal between each peak represents detection of light from disk 13 between each process chamber. The corresponding signal is integrated to produce histogram 264 which displays the detected signal from each of 96 process chambers. Control unit 23 integrates 16 samples from a process chamber in each of 16 rotations of disk 13. Histogram 264 therefore contains 256 samples of the contents in each samples process chamber. In some embodiments, software may automatically adjust offset control 268 by recognizing elements of the raw signal waveform. Message window 266 displays command information and error messages relating to optical control and light detection.

Figure 19:
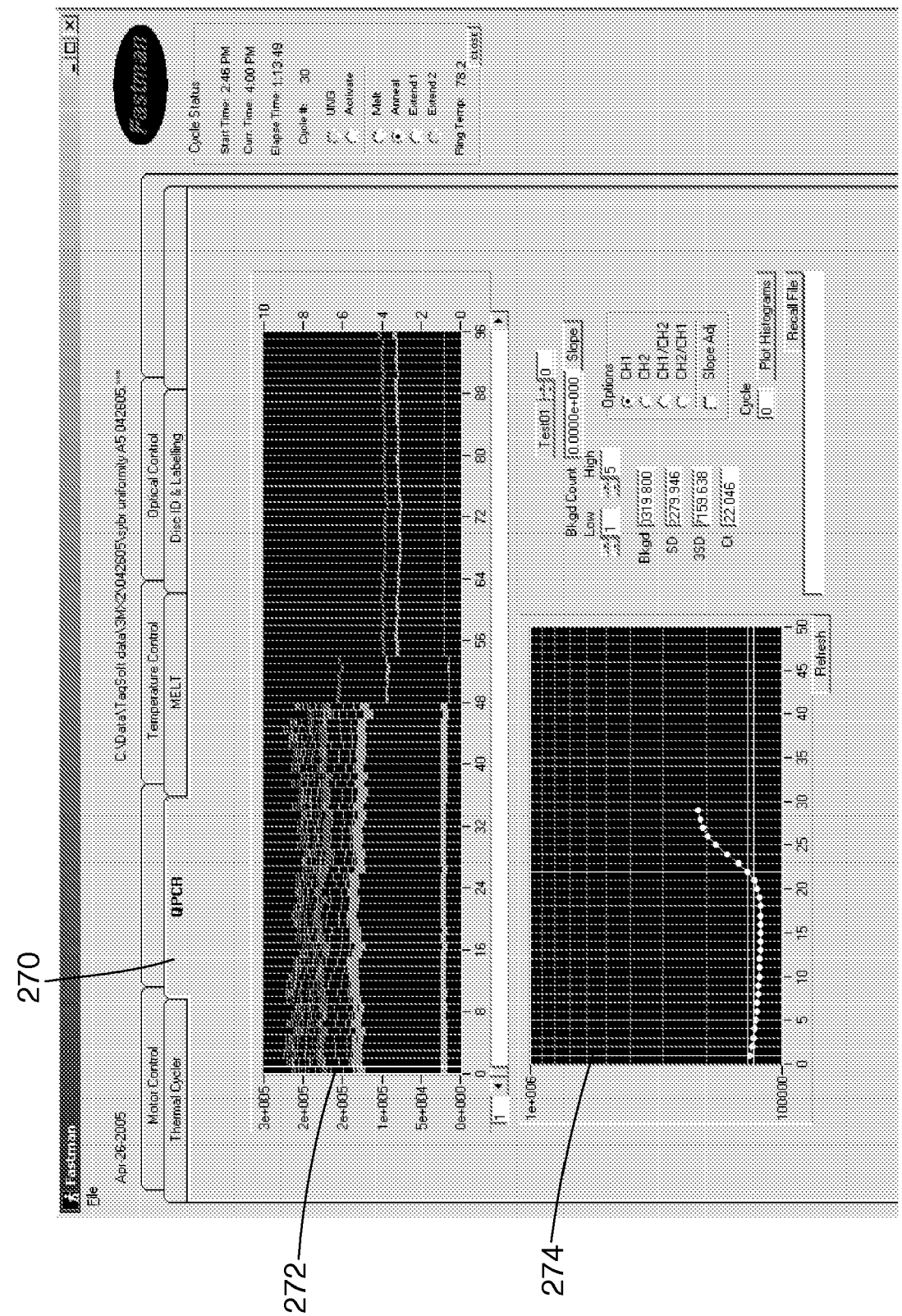
FIG. 19 is an exemplary screen shot of a real-time PCR user interface.

FIG. 19 is an exemplary screen shot of a real-time PCR user interface. Data screen 270 is highlighted and shows histogram 272 and product graph 274. Screen 270 shows the real-time data being collected from the process chambers of disk 13. Histogram 272 displays the integrated signal for each process chamber while product graph 274 displays the amount of amplified product as a function of cycle number. In other embodiments, results for the process chambers may vary under different applications.

Various embodiments of the invention have been described. These and other embodiments are within the scope of the following claims.

The invention claimed is:

1. A detection device comprising:
   a disk having a plurality of process chambers each holding a respective sample and at least one of two or more fluorescent dyes, wherein at least one of the process chambers holds two or more of the fluorescent dyes;
   a motor to rotate the disk;
   a plurality of optical modules; and
   a housing having a plurality of locations adapted to receive the optical modules, each of the plurality of locations having a respective fiber optic coupler mounted therein, wherein each of the plurality of optical modules are removable from the locations of the housing;
   wherein each of the optical modules includes an optical channel having a light source selected for a different one of the dyes, a lens to capture fluorescent light emitted from the disk, and an optical output port adapted to engage any of the fiber optic couplers mounted within the plurality of locations of the module housing, wherein in each of the optical modules the lens is optically coupled to the output port to deliver the fluorescent light collected by the lens to the optical output port of the optical module.

2. The detection device of claim 1, further comprising:
a detector; and
a fiber optic bundle coupled to the optical output port of each of the plurality of optical modules by the fiber optic couplers to convey the fluorescent light from the multiple optical modules to the detector.

3. The detection device of claim 1, further comprising a plurality of attachment mechanisms to attach each of the plurality of optical modules to the housing.

4. The detection device of claim 1, wherein each of the attachment mechanisms includes a lever, a pivot pin, a spring, a latch or a screw.

5. The detection device of claim 1, wherein each of the locations includes a set of one or more electrical contacts, and wherein each optical module has a set of one or more electrical contacts for electronically coupling to the electrical contacts of the locations when inserted into the housing.

6. The detection device of claim 5, further comprising a control unit, wherein the control unit controls the light source within each of the optical modules via the electrical contacts.

7. The detection device of claim 6, wherein each of the optical modules includes an electrical component that communicates with the control unit via the electrical contacts.

8. The detection device of claim 6, wherein the electrical contacts include a flex circuit connection.

9. The detection device of claim 7, wherein the electrical component of each of the optical modules outputs unique identification information for the respective optical module.

10. The detection device of claim 7, wherein the electrical component of each of the optical modules outputs information describing at least one optical characteristic of an optical component contained within the optical module.

11. The detection device of claim 7, wherein the electrical component includes programmable read-only memory (PROM), Flash, an internal storage medium or a removable storage medium.

12. The detection device of claim 7, wherein the electrical components include a laser source that emits a laser to open a valve separating a process chamber from a holding chamber on the disk.

13. The detection device of claim 7, wherein one or more of the optical modules includes a microprocessor.

14. The detection device of claim 1, wherein each of the plurality of optical modules further comprises an excitation filter and a detection filter.

15. The detection device of claim 1, wherein at least two of the optical modules are combined to form a removable multi-channel optical module having at least two separate optical channels having light sources selected for at least two different ones of the dyes, and wherein the removable multi-channel optical module occupies at least two of the locations within the housing.

16. The detection device of claim 1, further comprising a laser valve control system electrically coupled to one of the plurality of optical modules.

17. The detection device of claim 16, wherein the laser valve control system controls a laser within one of the optical modules to selectively open a valve separating a process chamber from a holding chamber on the disk.

18. The detection device of claim 1, wherein the light sources of the optical modules comprise light emitting diodes or laser diodes.

19. The detection device of claim 1, wherein the light sources are selected for detection of different species of a polymerase chain reaction (PCR) utilizing fluorescence detection at multiple wavelengths.

20. The detection device of claim 1, wherein the device includes at least four optical modules.

21. The detection device of claim 1, wherein the plurality of optical modules are aligned around the disk to sequentially interrogate one or more process chambers.

22. The detection device of claim 1, wherein two or more optical modules interrogate one or more process chambers without stopping the rotation of the disk.

23. The detection device of claim 1, wherein the plurality of optical modules are arranged so that each optical module detects samples at its associated radial position on the disk.

24. The detection device of claim 23, wherein at least two of the plurality of optical modules are positioned over different radial positions of the disk.

25. A detection system comprising:
a disk having a plurality of process chambers each holding a respective sample and at least one of two or more fluorescent dyes, wherein at least one of the process chambers of the disk holds two or more of the fluorescent dyes;
a data acquisition device; and
a detection device coupled to the data acquisition device, wherein the detection device comprises:
a motor to rotate the disk;
a plurality of optical modules, and
a housing having a plurality of locations adapted to receive the optical modules, each of the plurality of locations having a respective fiber optic coupler mounted therein, wherein each of the plurality of optical modules are removable from the locations of the housing;
wherein each of the optical modules includes an optical channel having a light source selected for a different one of the dyes, a lens to capture fluorescent light emitted from the disk, and an optical output port adapted to engage any of the fiber optic couplers mounted within the plurality of locations of the module housing, wherein in each of the optical modules the lens is optically coupled to the output port to deliver the fluorescent light collected by the lens to the optical output port of the optical module.

26. The system of claim 25, further comprising:
a detector; and
a fiber optic bundle coupled to the plurality of optical modules to convey the fluorescent light from the multiple optical modules to the detector.

27. The system of claim 26, wherein each of the locations includes a set of one or more electrical contacts, and wherein each optical module has a set of one or more electrical contacts for electronically coupling to the electrical contacts of the locations when inserted into the housing.

28. The system of claim 26, wherein the optical output port optically couples the optical module to a leg of the fiber optic bundle by engaging the fiber optical coupler of the location within which the optical module is positioned.

29. The system of claim 28, wherein the optical output port has a slidable connection that allows the leg of the fiber optic bundle to be slidably engaged and disengaged from the optical output port of the optical module.

30. The system of claim 29, further comprising a bias member associated with the slidable connection to force the leg of the fiber optic bundle against the optical output port.

31. The system of claim 28, wherein the optical output port has a threaded end for engaging a threaded connector of the leg of the fiber optic bundle.

32. The system of claim 25, further comprising a slot sensor trigger that provides an output signal for synchronization of rotation of the disk with the captured fluorescent light emitted from the disk.

33. The system of claim 32, further comprising a control unit that uses the slot sensor trigger output signal to compute a time offset between the modules, controls the light source within each of the optical modules and processes data from the captured fluorescent light emitted from the disk based on the time offset.

34. The system of claim 25, further comprising a laser valve control system electrically coupled to one of the plurality of optical modules.

35. The system of claim 34, wherein the laser valve control system controls a laser within one of the optical modules to selectively open a valve separating a process chamber from a holding chamber on the disk.

36. A detection device comprising:
a disk having a process chamber holding a sample and at least two or more fluorescent dyes;
a motor to rotate the disk;
one or more optical modules, and
a housing having a location adapted to receive one of the optical modules, the location having a fiber optic coupler mounted therein,
wherein each of the optical modules includes an optical channel having a light source selected for a different one of the dyes, a lens to capture fluorescent light emitted from the disk, and an optical output port adapted to engage the fiber optic coupler mounted within the location of the module housing, wherein the lens is optically coupled to the output port to deliver the fluorescent light collected by the lens to the optical output port of the optical module.

* * * * *